US009085634B2

(12) United States Patent
Rodriguez Mallon et al.

(10) Patent No.: US 9,085,634 B2
(45) Date of Patent: Jul. 21, 2015

(54) VACCINE COMPOSITION FOR CONTROLLING ECTOPARASITE INFESTATIONS

(75) Inventors: Alina Rodriguez Mallon, Ciudad de la Habana (CU); Erlinda Fernández Díaz, Ciudad de la Habana (CU); Mario Pablo Estrada Garcia, Ciudad de la Habana (CU); Yamila Carpio González, Ciudad de la Habana (CU)

(73) Assignee: Centro de Ingeniería Genética y Biotecnología, La Habana (CU)

( * ) Notice: Subject to any disclaimer, the term of this patent is extended or adjusted under 35 U.S.C. 154(b) by 0 days.

(21) Appl. No.: 13/825,892

(22) PCT Filed: Sep. 26, 2011

(86) PCT No.: PCT/CU2011/000005
§ 371 (c)(1),
(2), (4) Date: Mar. 25, 2013

(87) PCT Pub. No.: WO2012/041260
PCT Pub. Date: Apr. 5, 2012

(65) Prior Publication Data
US 2013/0273095 A1    Oct. 17, 2013

(30) Foreign Application Priority Data
Sep. 28, 2010 (CU) .................................. 2010-0188

(51) Int. Cl.
*A61K 39/00* (2006.01)
*A61K 39/002* (2006.01)
*A61K 39/385* (2006.01)
*C07K 14/435* (2006.01)

(52) U.S. Cl.
CPC ....... *C07K 14/43509* (2013.01); *A61K 39/0003* (2013.01); *C07K 14/43527* (2013.01)

(58) Field of Classification Search
None
See application file for complete search history.

(56) References Cited

U.S. PATENT DOCUMENTS 5,955,089 A * 9/1999 Briles et al. ................ 424/244.1
6,077,993 A * 6/2000 Mahajan ..................... 800/278

FOREIGN PATENT DOCUMENTS

WO   WO2004016586 A2   2/2004

OTHER PUBLICATIONS

Plotkin et al (Vaccines, W. B. Saunders Co. 1988, p. 571).*
Raynard et al (Pest Manag. Sci. vol. 58, pp. 569-575, 2002).*
Koff et al., "Inhibition of Dengue Virus Replication by Amantadine Hydrochloride", Antimicrobial Agents and Chemotherapty, vol. 18, No. 1, pp. 125-129 (Jul. 1980).
Schlegel et al., "Amantadine and Dansylcadaverine Inhibit Vesicular Stomatitis Virus Uptake and Receptor-Mediated Endocytosis of Alpha2-Macroglobulin", Proc. Natl. Acad. Sci., vol. 79, No. 7, pp. 2291-2295 (1982).
Database Geneseq [Online] Mar. 9, 2006, "West Nile Virus Envelope Protein Ectodomain Peptide 39", XP002453298 retrieved from EBI accession No. GSP:AEF13619 Database accession No. AEF13619.
Database Geneseq [Online] Sep. 3, 1992, "DEN1 E Glycoprotein (373-398)", XP0024153499 retrieved from EBI accession No. GSP:AAR25390 Database accession No. AAR25390.
Cabrera-Hernandez et al., "Mammalian Dengue Virus Receptors", Dengue Bulletin, vol. 29, pp. 119-135 (2005).
Wojda et al., Protein kinases CKI and CKII are implicated in modificaiton of ribosomal proteins of the yeast *Trichosporon cutaneum*, Acta Biochimica Polonica, vol. 49, No. 4, pp. 947-957 (2002).
Skeiky et al., *Trypanosoma cruzi* Acidic Ribosomal P Protein Gene Family, Journal of Immunology, vol. 151, pp. 5504-5515 (1993).
Iborra et al., The *Leishmania infantum* Acidic Ribosomal Protein P0 Administered as a DNA Vaccine Confers Protective Immunity to *Leishmania* major Infection in BALB/c Mice, Infection and Immunity, vol. 71, No. 11, pp. 6562-6572 (2003).
Wikel et al., Arthropod Modulation of Host Immune Responses, The Immunology of Host-Ectoparasitic Arthropod Relationships, (1996).
Lees et al., Factors associated with changing efficacy of emamectin benzoate against infestations of *Lepeophtheirus salmonis* on Scottish salmon farms, Journal of Fish Diseases, vol. 31, pp. 947-951 (2008).
Denholm et al., Analysis and management of resistance to chemotherapeutants in salmon lice, *Lepeophtheirus salmonis* (Copepoda: Caligidae), Pest Manag. Sci., vol. 58, pp. 528-536 (2002).
Yasser Ezzat Shahein, Molecular cloning and expression of a larval immunogenic protein from the cattle tick *Boophilus annulatus*, Veterinary Immunology and Immunopathology, vol. 121, pp. 281-289 (2008).
V. Ragias, et al., Incidence of an intense *Caligus minimus* Otto 1821, *C. pageti* Russel, 1925, *C. mugilis* Brian, 1935 and *C. apodus* Brian, 1924 infection in lagoon cultured sea bass (*Dicentrarchus labrax* L.) in Greece, Aquaculture, vol. 242, pp. 727-733 (2004).
Rajeshwari et al., The P Domain of the P0 Protein of *Plasmodium falciparum* Protects against Challenge with Malaria Parasites, Infection and Immunity, vol. 72, No. 9, pp. 5515-5521 (2004).

(Continued)

*Primary Examiner* — Albert Navarro
(74) *Attorney, Agent, or Firm* — Hoffmann & Baron, LLP

(57) ABSTRACT

The present invention relates to the use of a peptide of P0 ribosomal protein in the manufacture of a vaccine composition to control of ectoparasite infestations and therefore the transmission of their associated pathogens. This peptide is located between 267 and 301 amino acids of the P0 protein, and can be obtained by recombinant means or by chemical synthesis. This peptide can be fused to a carrier protein or peptide, or an immuno-carrier and be included in an oily formulation. The formulations comprising the peptide vaccine confer protection against ticks and ectoparasites known as "sea lice" without generating autoimmunity in the host organism. Among these ticks may be mentioned species as *Rhipicephalus microplus*, *Rhipicephalus sanguineus* and *Ixodes scapularis*, and between sea lice are those of the *Caligus* and *Lepeophtheirus* genera.

10 Claims, 7 Drawing Sheets

(56) References Cited

OTHER PUBLICATIONS

Figure 1:
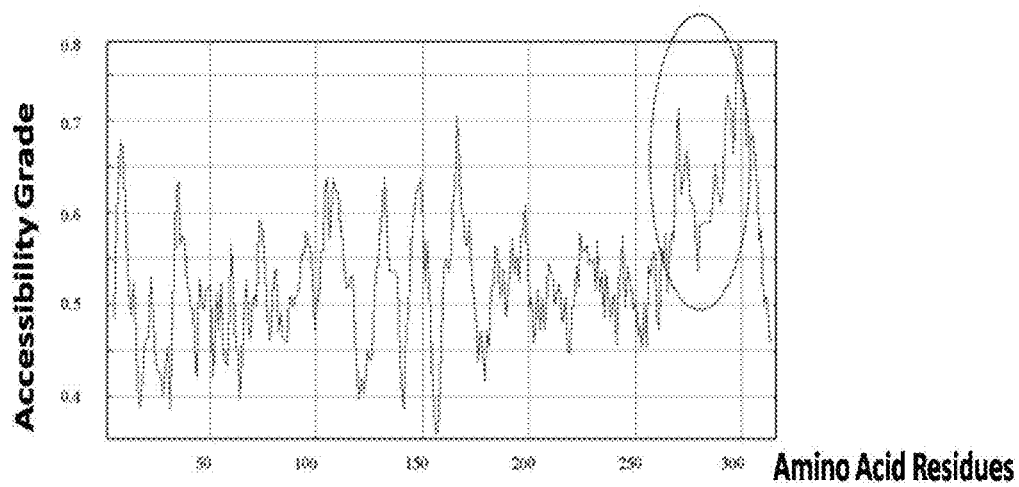

Pike et al., Sealice on Salmonids: Their Biology and Control, Advances in Parasitology, vol. 44, (1999).

Parola et al., Tick-borne bacterial diseases emerging in Europe, Clin Microbiol Infect, vol. 7, pp. 80-83 (2001).

Barker et al., Preliminary studies on the isolation of bacteria from sea lice, *Lepeophtheirus salmonis*, infecting farmed salmon in British Columbia, Canada, Parasitol Res., vol. 105, pp. 1173-1177 (2009).

Karin Boxaspen, A review of the biology and genetics of sea lice, Journal of Marine Science, vol. 63, pp. 1304-1316 (2006).

Haiyan Gong, et al., Gene silencing of ribosomal protein P0 is lethal to the tick *Haemaphysalis longicornis*, Veterinary Parasitology, vol. 151, pp. 268-278 (2008).

Salvador Iborra, et al., Vaccination with the *Leishmania infantum* Acidic Ribosomal P0 Protein plus CpG Oligodeoxynucleotides Induces Protection against Cutaneous Leishmaniasis in C57BL/6 Mice but Does not prevent Progressive Disease in BALB/c Mice, vol. 73, No. 9, pp. 5842-5852 (2005).

Sanchita Chatterjee et al., Antibodies against Ribosomal Phosphoprotein P0 of *Plasmodium falciparum* Protect Mice against Challenge with *Plasmodium yoelii*, Infection and Immunity, vol. 68, No. 7, pp. 4312-4318 (2000).

Stewart C. Johnson, et al., A Review of the Impact of Parasitic Copepods on Marine Aquaculture, Zoological Studies, vol. 43, pp. 229-243 (2004).

Sandra Bravo et al., Sensitivity assessment of *Caligus rogercresseyi* to emamectin benzoate in Chile, Aquaculture, vol. 282, p. 7-12 (2008).

Terkawi et al., A shared antigen among Babesia species: ribosomal phosphoprotein P0 as a universal babesial vaccine candidate, Parasitol Res, vol. 102, pp. 35-40 (2007).

Terkawi et al., *Babesia gibsoni* ribosomal phosphoprotein P0 induces cross-protective immunity against B-microti infection in mice, Vaccine, vol. 25, pp. 2027-2035 (2007).

Fuente et al., Vaccination against ticks (*Boophilus* spp.): the experience with the Bm86-based vaccine Gavac, Genetic Analysis: Biomolecular Engineering, vol. 15, pp. 143-148 (1999).

Zhang et al., Identification of ribosomal phosphoprotein P0 of *Neospora caninum* as a potential common vaccine candidate for the control of both neosporosis and toxoplasmosis, Molecular and Biochemical Parasitology, vol. 153, pp. 141-148 (2007).

* cited by examiner

VACCINE COMPOSITION FOR CONTROLLING ECTOPARASITE INFESTATIONS

CLAIM OF PRIORITY

This application is the U.S. National Phase of, and Applicants claim priority from, International Application Number PCT/CU2011/000005 filed Sep. 26, 2011 and Cuban Patent Application No. 2010-0188 filed Sep. 28, 2010, which are incorporated herein by reference.

FIELD OF THE INVENTION

The present invention falls within the field of veterinary medicine, in particular the control of ectoparasite infestations and their associated pathogens transmission. This control is achieved by using a peptide of the ribosomal protein P0 in the manufacture of vaccine compositions. The vaccine formulations comprising the peptide confer protection without generating autoimmunity in the host organism.

STATE OF THE PRIOR ART

Terrestrial bloodsucking ectoparasites such as mosquitoes, fleas and ticks are vectors for transmission of infectious agents causing diseases. Some of these diseases directly affect human and/or their affective animals, while others are causing great economic losses in the agricultural field. Examples of diseases transmitted by ectoparasites are malaria, leishmaniasis, dengue fever, ehrlichiosis and Lyme disease. Ticks are considered the second transmitter of diseases to humans after mosquitoes (P. Parola and D. Raoult, Clin. Microbiol. Infect. 2001, 7: 80-83). Haemoparasitic infections transmitted by ticks cause annual losses in the order of billions of U.S. dollars in the livestock industry, primarily affecting cattle production in tropical and subtropical areas. Among the diseases most important in this regard include anaplasmosis, babesiosis, Lyme disease (caused by *Borrelia burdogferi*) and the so-called East Coast fever (*Theileria parva* produced).

Ectoparasites known as sea lice (*Copepoda, Caligidae*) are the most widespread marine pathogen in the last 30 years in the salmon industry, ranging over the past 15 years other species of farmed fish and wild stocks of salmonids (Pike, A W and Wadsworth, S L Advances in Parasitology 2000, 44:233-337, Ragi, V. et al. Aquaculture 2004, 242: 727-733). The economic losses are caused by organisms of the genera *Caligus* and *Lepeophtheirus*. The so-called sea lice can cause physiological changes in their hosts, including the development of a stress response, reduced immune function, osmoregulation failure and death if untreated infection (Johnson, S C, et al. Zool Studies 2004, 43: 8-19). There is also some evidence to suggest that sea lice could be vectors for transmission of infections caused by viruses and bacteria to fish (Barker, E D, et al. Parasitology Research 2009, 105: 1173-1177).

A wide variety of chemicals and drugs have been used to control tick infestations and sea lice. The use of chemical pesticides as amidines, organophosphates, hydrogen peroxide and other currently constitutes the fundamental measure to control these ectoparasites. However, the intensive use of these chemicals has drawbacks as the contamination of food (fish, meat and milk), environmental pollution and development of resistance by ectoparasites (Y E Shahein Vet. Immunol. And Immunopathol. 2008, 121: 281-289, Denholm, I. Pest Manag Sci 2002, 58: 528-536, Bravo, S. et al. Aquaculture 2008, 282: 7-12, Lees et al. J. Fish Dis. 2008, 31: 947-951).

Vaccination is considered a promising alternative for controlling infestations by ectoparasites from the standpoint of efficacy, environmental safety and economic sustainability. The feasibility of using antigens produced by recombinant DNA techniques for this purpose has been demonstrated with Bm86-based commercial vaccines against *Rhipicephalus microplus* tick (TickGARD, Hoechst Animal Health, Australia, and Gavac marketed by Heber Biotec, Cuba). The latter has proven effective in field studies where the application is included within an integrated control program. In the case of sea lice there are some advances in the use of proteins as vaccine candidates, as is the case of akirin-2 of *Caligus rogercresseyi*, which is called my32. Challenging trials with my32 have been performed with promising results (Patent Application WO2008/145074 "Sequences of nucleic acids and amino acids, and vaccine for the control of infestations by ectoparasites in fish").

Identification of novel protective antigens is the limiting step in increasing the effectiveness of these vaccines. Although emerging tick proteins have been identified recently, and have been proposed as potential protective molecules, only a limited number of them have been evaluated in vaccine trials as antigens produced by recombinant DNA techniques. In the case of sea lice which are ectoparasites that feed on mucus, skin and blood of the host and therefore have only limited contact with the host immune system (Boxaspen, K. ICES Journal of Marine Science 2006, 63: 1304-1316) have been investigated as vaccine candidates, the parasite immunomodulatory proteins that suppress the host immune response in the adhesion and feeding sites (Wikel, S K et al. "Arthropod modulation of host immune responses". In: The Immunology of Host-Ectoparasiticide Arthropod Relationships. Editors: Wikel, S K, CAB Int, 1996, pp. 107-130). Have also studied other vitellogenin-like molecules and adhesion proteins to the host (Johnson, S C et al. Zool Studies 2004, 43: 8-19; Boxaspen, K. ICES Journal of Marine Science 2006, 63: 1304-1316) but due to poor knowledge of the mechanisms and pathology of the salmon infestation by sea lice, targets identification for prevention and treatment of this infection have not been successful. However, the research results in the evaluation of different vaccine candidates in immunization trials have shown that the combined use of several molecules involved in different physiological processes, is a feasible method to control ectoparasite infestations.

Eukaryotic ribosomes are composed of individual molecules of ribosomal RNA (rRNA) and more than 80 proteins organized into major and minor subunits. Most ribosomal proteins are basic (isoelectric point (pI)>8.5), but there is also a group of acidic proteins (pI=3.0 to 5.0) whichs form a stalk-like structure in the largest ribosome subunit. These acidic proteins are called P proteins (P0, P1 and P2), due to its ability to be phosphorylated, which plays a fundamental role in regulating translational activity of ribosomes (Wojda I. et al. Acta biochar. Pol. 2002, 49: 947-957). P proteins contain a conserved C-terminal region of about 17 amino acids, whose last six residues are highly conserved, which forms the basis of immunological cross-reactivity between them and the P proteins of other species. The P0 protein is essential for the assembly of 60S ribosomal subunit. P0 binds directly to P1, P2, 28S rRNA and the factor eEF2. Its absence leads to the generation of deficient ribosomes of the 60S subunit, which are inactive for protein synthesis, leading to cell death.

The P proteins are highly immunogenic and have been extensively studied in humans because of its association with autoimmune diseases and carcinogenesis. These applications of ribosomal proteins have been protected by patents by their respective authors. The ribosomal protein P0, in particular, is a promising vaccine candidate against several protozoa and bacteria. It was immunogenic as recombinant antigen (either using the whole protein or C-terminal region consisting of the last 11-16 amino acids) or by naked DNA immunization against *Toxoplasma gondii*, *Neospora caninum* (H. Zhang et al. Mol. Biochem. Parasitol 2007, 153: 141-148), *Trypanosoma cruzi* (Skeiky Y A et al. J. Immunol. 1993, 151: 5504-5515), *Leishmania infantum* (S. Iborra et al., Infect. Immunol. 2003, 71: 6562-6572 and 2005, 72: 5515-5521) and several species of *Babesia* (Terkawi M A et al., Vaccine 2007, 25: 2027-2035; Terkawi M A et al. Parasitol. Res 2007, 102: 35-40) and *Plasmodium* (S. Chatterjee et al. Infect. Immunol. 2000, 68: 4312-4318; Rajeshwari K. et al. Infect. Immunol. 2004, 72: 5515-5521). The immune response obtained in most of these experiments was characterized by the generation of high titers of specific antibodies, capable of conferring active and passive protection against infection, activation of T lymphocytes and the gamma interferon production (IFNγ) as part of a Th1 response pattern.

Its use as an immunogen against various bacteria and protozoa, without the report of autoimmune reactions in the host was due to the relatively low amino acid sequence identity of this protein between these microorganisms and mammals. The most striking case was the immunization of mice with a peptide consisting of the last 16 amino acids of P0ribosomal protein of *Plasmodium falciparum* (Rajeshwari K. et al., Infect. Immunol. 2004, 72: 5515-5521), which presents 68% identity with the C-terminus of this same protein in mice. However, the use of this whole protein or its C-terminal region as immunogens to control ticks and sea lice infestations is limited by the high degree of amino acid identity that exists for this antigen among ectoparasites and their host organisms.

Recent experiments with specific interference RNA silencing expression of this protein in *Haemaphysalis longicornis* ticks showed a significant decrease in weight gain of ticks, and a mortality of 96%, caused by structural level affectations of salivary gland and cuticle, suggesting that P0 ribosomal protein is necessary for the ingestion of blood and viability of ticks and possibly of other ectoparasites (Gong H et al. Vet. Parasitol. 2008, 151: 268-278). However, the development of a vaccine candidate based on this antigen has as drawbacks the high degree of identity between the reported sequences of host vertebrates and his ectoparasites such as ticks and sea lice, which is higher in the C-terminus of the protein. This can result in the induction of tolerance or the generation of autoantibodies in the host organism.

The intensive use of chemicals and drugs to control infestations of ticks and sea lice has drawbacks as the contamination of food with chemical residues, environmental pollution and the development of resistance by ectoparasites. Therefore, vaccination is considered a promising alternative and there is a need to identify new vaccine antigens that are capable of conferring protection by itself or can be incorporated into existing vaccines.

SUMMARY OF THE INVENTION

The present invention solves the above problem by providing a vaccine composition for the control of infestations by ectoparasites comprising a peptide of the P0 ribosomal protein of these ectoparasites. This composition comprises as antigen, an immunogenic region of the P0 ribosomal protein that is little conserved among ectoparasites and the organisms affected by them, according to results of a study to be disclosed in this invention, the first time. The region identified in the P0 ribosomal protein is between 267 and 301 amino acids of the same.

The presence of P0 protein in all organisms as a structural component of ribosomes and essential for cell viability is an advantage for the use of these sequences with the objective to obtain vaccine candidates against different species of ectoparasites. However, the use of this protein or its C-terminal region as immunogen to control infestations of ticks and sea lice is limited by the high degree of amino acid identity that exists for this antigen among ectoparasites and their host organisms.

This situation is avoided for the first time in this invention, by identifying highly immunogenic regions within the protein, which coincide with areas of low sequence similarity between these groups of organisms. By bioinformatics' predictions, it was found that this region coincides with an area of low hydrophobicity and high degree of accessibility of protein, which makes likely this amino acid sequence to be exposed.

Complementary DNAs (cDNA) were generated by reverse-transcription starting from total RNA of *Rhipicephalus microplus* and *R. sanguineus* larvae and adult sea lice from *Caligus rogercresseyi* specie. The nucleotide sequences encoding P0 ribosomal protein of these ticks (SEQ ID NO. 1 and SEQ NO. 2) and that sea lice were amplified by Polymerase Chain Reaction (PCR) using these cDNAs and specific oligonucleotides.

The polypeptide sequences for P0 protein of ectoparasites *R. microplus* and *R. sanguineus* were identical between them, and were designated as SEQ ID NO. 3. This sequence and that of the *C. rogercresseyi's* P0 showed a sequence identity greater than 70% with the P0 proteins of its host organisms, while still higher for the last 16 amino acids of the C-terminal, described as the most immunogenic within the protein. The lesser similarity area in amino acid sequence, which in turn is likely to be exposed and be immunogenic, was detected in all cases in the region between amino acids 267 and 301 (SEQ ID NO.4, peptide corresponding P0 protein of *Rhipicephalus microplus* [pP0] SEQ ID NO.6, peptide corresponding P0 protein of *Ixodes scapularis* [pP0Is] SEQ ID NO.8, peptide corresponding P0 protein of *Caligus clemensi* [pP0Cc], SEQ ID No.9, peptide corresponding P0 protein of *L. salmonis* [pP0Ls] and SEQ ID NO.10, peptide corresponding P0 protein of *C. rogercresseyi* [pP0Cr]).

Therefore, in one embodiment of the invention, the vaccine composition comprises a peptide with an amino acid sequence identified as SEQ ID NO. 4, SEQ ID NO. 6, SEQ ID NO. 8, SEQ ID NO. 9 or SEQ ID NO. 10, a fragment of those sequences, or a peptide or polypeptide that exhibits at least 70% identity with such sequences. The present invention relates also to those vaccine compositions where the indicated P0 peptide is fused, is combined or co-administered with another molecule, to increase their immunogenicity or enhance their protective effect. Such molecules are carrier proteins and immune-carriers. In one embodiment of the invention, this molecule is selected from the group consisting of hemocyanin, T-cell epitopes, the proteins that form virus-like particles, Bm86 protein from the *R. microplus* tick, the Rs86 protein from the *R. sanguineus* tick and my32 protein of *C. rogercresseyi* or *L. salmonis*. sea lice.

The peptides identified as SEQ ID NO. 4, 6, 9 and 10, between 35 and 36 amino acids, and 20 amino acids fragments of these were obtained by chemical synthesis and conjugated to hemocyanin (Keyhole Limpet Hemocyanin English, abbreviated as KLH) of *Megathura crenulata*, to enhance immunogenicity. Immunization experiments with challenge under controlled conditions were conducted with these conjugates to assess their protective capabilities. P0 peptide (pP0-SEQ ID NO. 4) was tested against *R. sanguineus* and *R. microplus* in rabbits and cattle, respectively. pP0Is (SEQ ID NO. 6) was evaluated against *I. scapularis* in rabbits. For its part, the peptides pP0Ls and pP0Cr (SEQ ID NO. 9 and SEQ ID NO.10, respectively) were evaluated against *L. salmonis* and *C. rogercresseyi*, respectively, both in *Salmo salar*.

Immunization of rabbits and cattle with the vaccine formulation containing the protein conjugate (pP0-KLH) and adjuvant Montanide 888 was able to induce a strong specific humoral immune response against the peptide in both cases. There was no evidence of the occurrence of an autoimmune specific response in experimental animals used, which was triggered by the recognition and reactivity of the P0 protein of these mammals by the antibodies generated against the pP0 peptide. This was confirmed by an "in vitro" cross-reactivity test in the RK-13 cell line of rabbit kidney, using hyperimmune serum against the peptide obtained in mice. Vaccinations with pP0-KLH conjugate induced protection against infestations by *R. sanguineus* and *R. microplus*, causing structural damages and affected biological parameters in both species of ticks. In addition, similar results were obtained against *I. scapularis* ticks after immunization with the synthetic peptide of the P0 protein of this tick (pP0Is) conjugated to hemocyanin.

The vaccination of salmon with pP0Ls-KLH and pP0Cr-KLH conjugates induced protection against infestations by both species of sea lice, as evidenced by a significant decrease in the number of parasites per fish. Immunization experiments were also conducted with pP0 and pP0Cr obtained by recombinant techniques, fused to the T epitopes of tetanus toxin and the fusion protein of measles virus (Measles Virus Fusion English protein, abbreviated MVF) in the same gene construct. As a result of immunization experiments with these chimeric antigens, in the case of sea lice, we found that fusion to the promiscuous T epitopes significantly improves the protection in comparison with antigen conjugated to KLH.

The pP0 was also fused to virus-like particles (VLPs) of Rabbit Hemorrhagic Disease Virus (RHDV), and found further that when the P0 peptide is fused to Bm86 antigen, the protective effect of the peptide is enhanced. This could be due to the combined effect of the antibodies produced against both immunogens and/or the fact that the structural damage caused by antibodies directed against the Bm86 antigen, at the gut of ticks, facilitates the action of specific antibodies against the peptide of P0 ribosomal protein. On the other hand, pP0Cr was fused to the my32 protein in another gene construct, and in this case, the most relevant effects on damages to *C. rogercresseyi* were obtained, presumably by enhancing of the individual specific effect of the two antigens.

Thus, in the invention was demonstrated that the vaccine compositions based on the pP0 peptide are effective for controlling infestations by ectoparasites such as ticks and sea lice. Therefore, pP0 based compositions are also useful for controlling the transmission of pathogens associated with these ectoparasites.

This vaccine comprises immunologically effective amount of antigen in a pharmaceutically acceptable adjuvant, by which to control infestations by these pathogens. As stated, the antigen in this vaccine is a peptide of the P0 ribosomal protein of these ectoparasites, between 267 and 301 amino acids, which corresponds to the region of least similarity in the amino acid sequence of the ectoparasite protein with the same region of the protein in their respective host organisms. This peptide is obtained by recombinant techniques or by chemical synthesis. Fused polypeptides comprising the P0 peptide can also be obtained by recombinant techniques. As known to those versed in this field of technology, the production of such antigens by recombinant means can use an expression system in yeast, bacteria, plants, insect larvae, insect cells or mammalian cells.

In one embodiment of the invention, the vaccine compositions may further comprise a vaccine adjuvant. In the context of the invention, vaccine formulations were evaluated comprising an oily adjuvant type. However, as adjuvants can be used aluminum salts, liposomal vesicles, immune system related molecules such as cytokines, among others.

The compositions of the invention can be administered in many different ways. In one embodiment of the invention, the composition is administered by injection. In another embodiment, formulations are administered through feed. In the event that the compositions are administered to fish can be applied using immersion baths.

Another object of the present invention is a vaccine composition for controlling infestations by ectoparasites comprising nucleic acids encoding the peptide of P0 ribosomal protein of these ectoparasites, corresponding to the region between 267 and 301 amino acids of the protein, and generates an immune response against the peptide by immunization with naked DNA. In one embodiment of the invention, this peptide has an amino acid sequence identified as SEQ ID NO. 4, SEQ ID NO. 6, SEQ ID NO. 8, SEQ ID NO. 9 or SEQ ID NO. 10, or it is a fragment of those sequences, or a peptide or polypeptide that exhibits at least 70% identity with such sequences.

The invention also relates to the use of the region between 267 and 301 amino acids of P0 ribosomal protein of ectoparasites in the manufacture of a vaccine composition to control infestations by these parasites or pathogens associated to them. In one embodiment, said peptide has an amino acid sequence identified as SEQ ID NO. 4, SEQ ID NO. 6, SEQ ID NO. 8, SEQ ID NO. 9 or SEQ ID NO. 10, or it is a fragment of those sequences, or a peptide or polypeptide that exhibits at least 70% identity with such sequences.

Advantages of the Proposed Solution

The present invention demonstrates the protective capacity of a vaccine formulation, which contains a peptide between amino acids 267 and 301 of the P0 ribosomal protein of different ectoparasites, against ticks as *R. microplus, R. sanguineus* and *I. scapularis*, and ectoparasites known as *L. salmonis* and *C. rogercresseyi* sea lice, without the occurrence of cross-react with the same protein in the host organisms. In all immunizations, the pP0 was administered conjugated or fused to an immune-carrier molecule to enhance the immune response of animals. In the case of ticks, the application of this peptide (or fragments thereof) fused to the Bm86 protein or combined with it, induces a greater damage on the viability and biological parameters of these arthropods than the damages caused by antigens when used individually. Therefore, the application of this chimera protein or combination of them as part of an integrated control program, could result in greater control of infestations by these or other tick species as well as in reducing the incidence of tick borne haemoparasitic diseases. In the case of sea lice, the greatest damages was observed when the pP0Cr was fused to promiscuous T epitopes and my32 protein. The high conservation degree of the peptide amino acid sequence among most arthropod species and sea lice, and low identity of this sequence with the corresponding fragment of the protein in mammals and fish, makes this peptide of P0 ribosomal protein (or fragments thereof) an antigen for the development of vaccines against ectoparasites.

BRIEF FIGURE DESCRIPTIONS

FIG. 1. Prediction of the accessibility degree of amino acid residues in the P0 ribosomal protein of R. microplus and R. sanguineus. The region corresponding to the sequence defined as SEQ ID NO.4 is marked with a circle.

Figure 2:
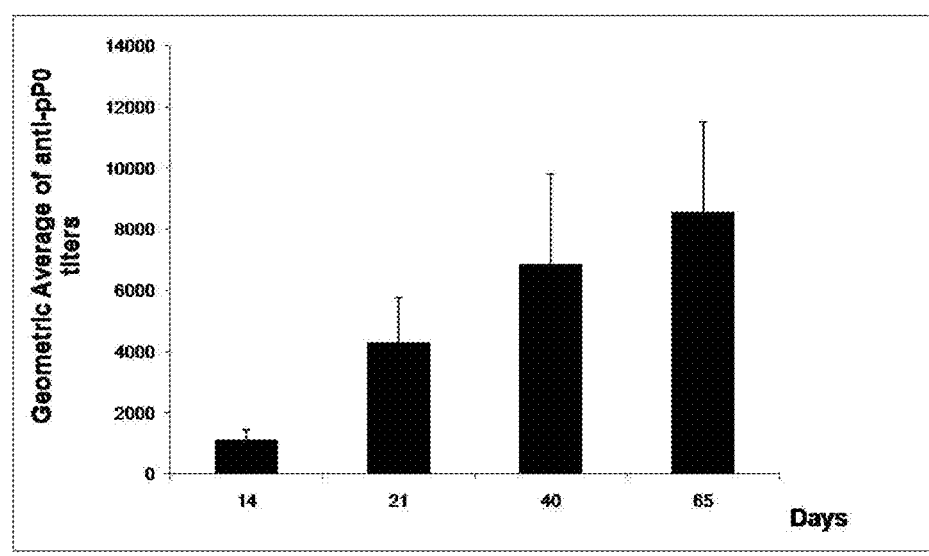

FIG. 2. Anti-P0 peptide specific IgG antibody response, detected by ELISA in serum of BALB/c mice immunized with the conjugate pP0-KLH. Data are expressed as the reciprocal of the antibody titer average, determined as the last serum dilution with an average optical density (OD) greater than three times the mean OD of negative serum. Standard deviations are represented by error bars in the positive direction. No antibody titers were detected for any animals on day zero.

Figure 3:
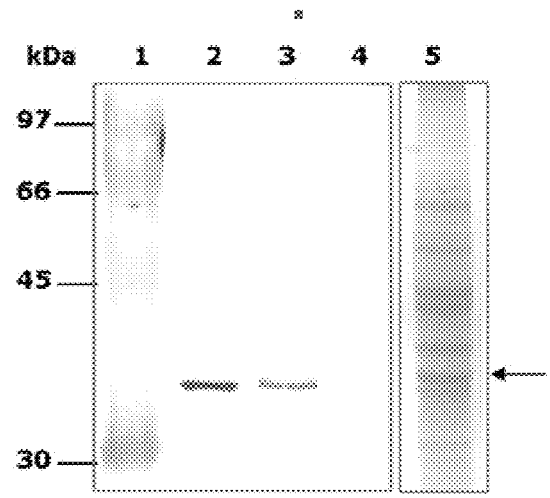

FIG. 3. Expression Pattern of P0 ribosomal protein of Rhipicephalus ticks in RK-13 rabbit cell line analyzed by Western blotting with polyclonal antibody generated in mice against P0. 1. Molecular weight standard, 2. Lysate of RK-13 cells transfected with pAdTrack-P0Rs plasmid under reducing conditions, 3. Lysate of RK-13 cells transfected with pAdTrack-P0Rs plasmid in non-reducing conditions, 4. Lysate of RK-13 cells non transfected under reducing conditions, 5. Polyacrylamide gel electrophoresis in the presence of sodium Dodecilosulfato (SDS-PAGE) under reducing conditions of the RK-13 cells lysate transfected with the plasmid pAdTrack-P0Rs.

Figure 4:
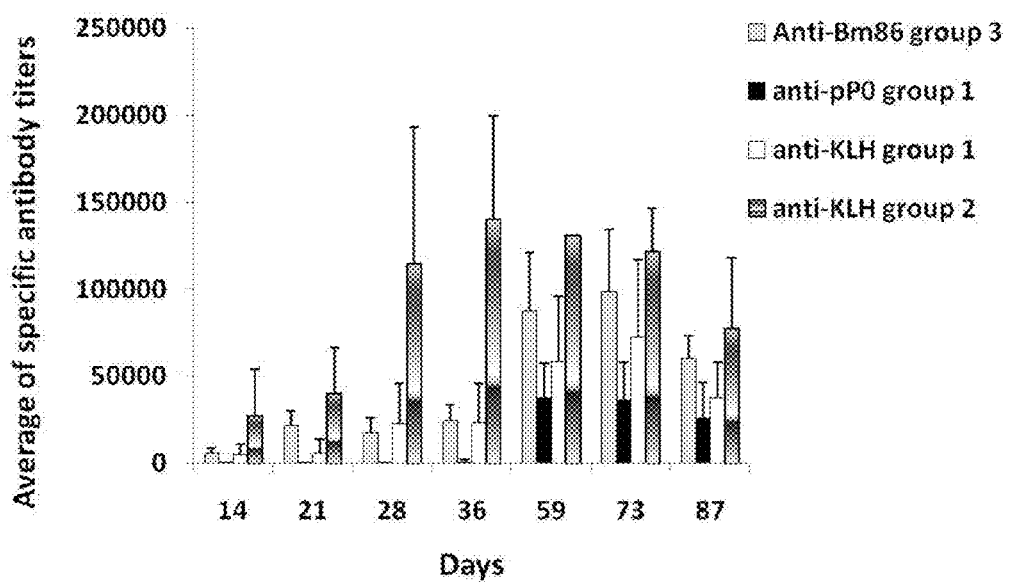

FIG. 4. Anti-KLH, anti-peptide P0 and anti-Bm86 IgG antibody responses detected by ELISA in serum from rabbits immunized with these antigens (Example 6). Data are expressed as the reciprocal of the average of antibody titer, determined as the last serum dilution with an average OD greater than three times the average OD of negative control groups according the case. Standard deviations are represented by error bars in the positive direction. Specific antibody titers against the antigens were not detected for any animals on day zero of the trial.

Figure 5:
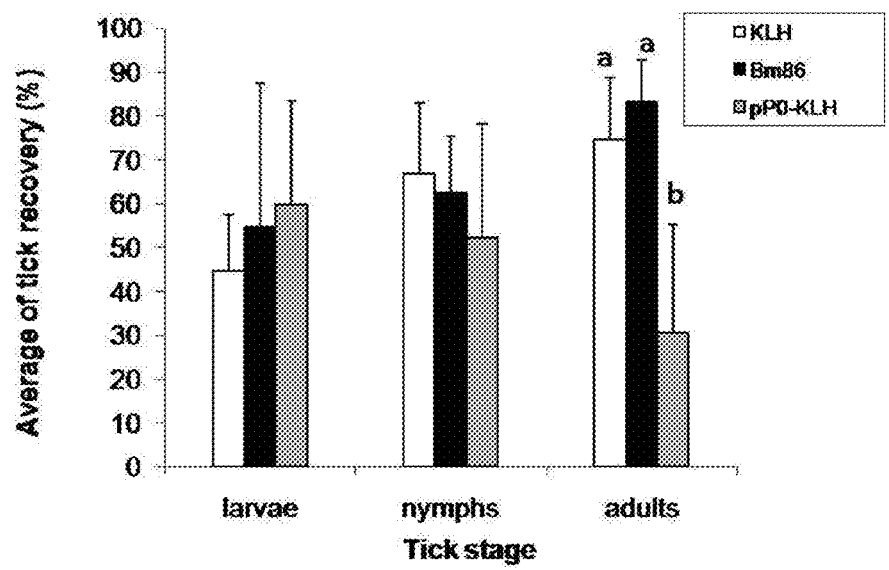

FIG. 5. Recovery of R. sanguineus larvae, nymphs and adults in rabbits immunized in Example 6. Data are expressed as the average percentages of larvae, nymphs and adults recovered in the different experimental groups. The standard deviations of the groups are represented by error bars in the positive direction. Different letters represent statistically significant differences between the experimental groups (ANOVA and Bonferroni multiple comparison test [P<0.01]. For the analysis, proportions data were previously transformed to arcsine of its square root).

Figure 6:
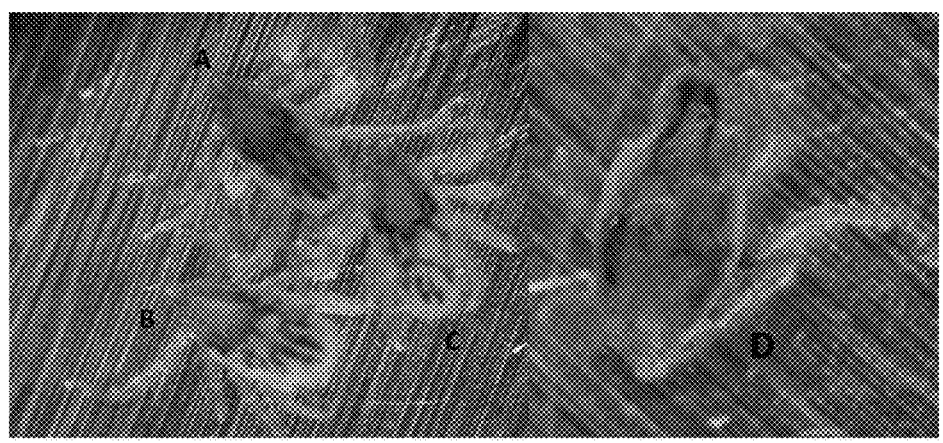

FIG. 6. Newly molted nymphs of R. sanguineus from larvae fed on different experimental groups of Example 6. (A) Negative control group (B) Immunized with Bm86 (C) Immunized with the conjugate pP0-KLH and (D) Appearance of dead nymphs molted from larvae fed on rabbits immunized with pP0-KLH.

Figure 7:
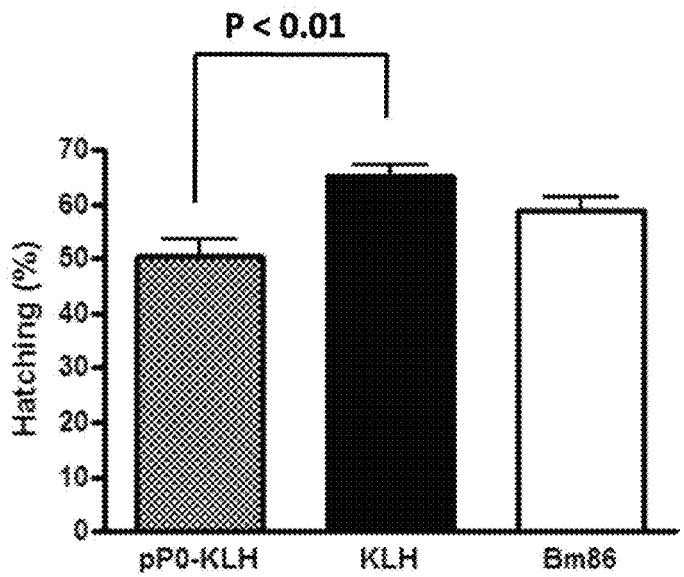

FIG. 7. Aoves hatch percent of R. sanguineus from teleoginas fed on rabbits immunized in Example 6. Data are expressed as the mean per group. The standard deviations for each group are represented by error bars in the positive direction. Significant differences are indicated by an asterisk (ANOVA and Bonferroni multiple comparison test (p<0.05).

Figure 8:
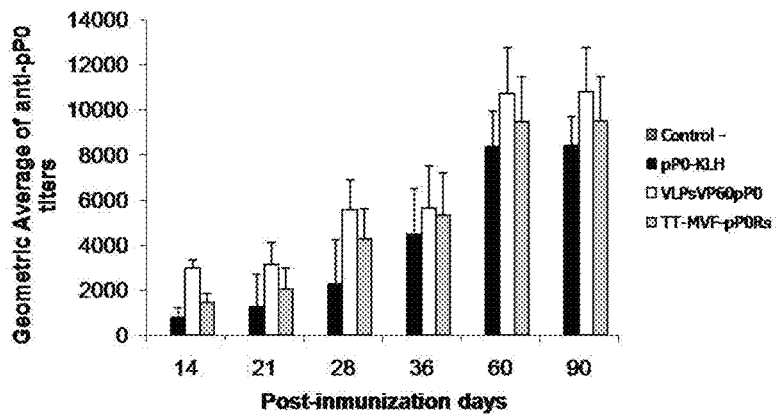
Figure 8:
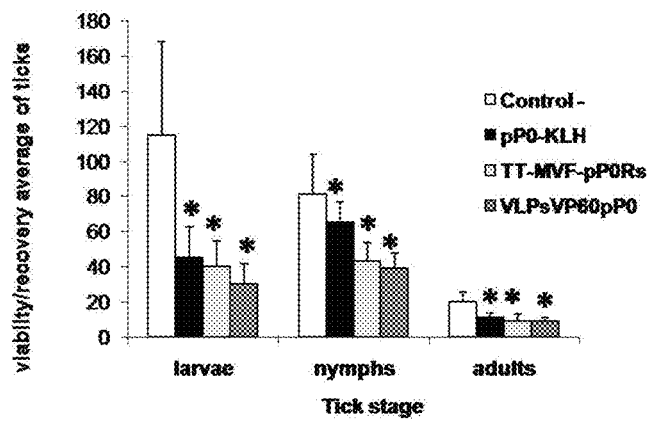

FIG. 8. Anti-P0 peptide IgG antibody response (A) and survival of R. sanguineus larvae, nymphs and adult (B) for the rabbits immunized with variants of this peptide fused to different immune-carrier molecules. Standard deviations are represented by error bars in the positive direction.

Figure 9:
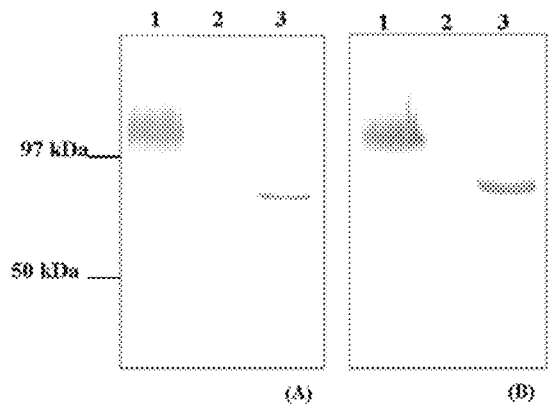

FIG. 9. Expression pattern of the Bm86-pP0 chimeric protein in the P. pastoris MP36 strain rupture precipitate analysed by Western blotting using hyperimmune sera generated against the peptide pP0 (A) and against the Bm86 protein (B). In both cases, line 1. Rupture precipitate under reducing conditions, 2. Rupture precipitate in non-reducing conditions, 3. Deglycosylated protein by digestion with the PNGase F enzyme.

Figure 10:
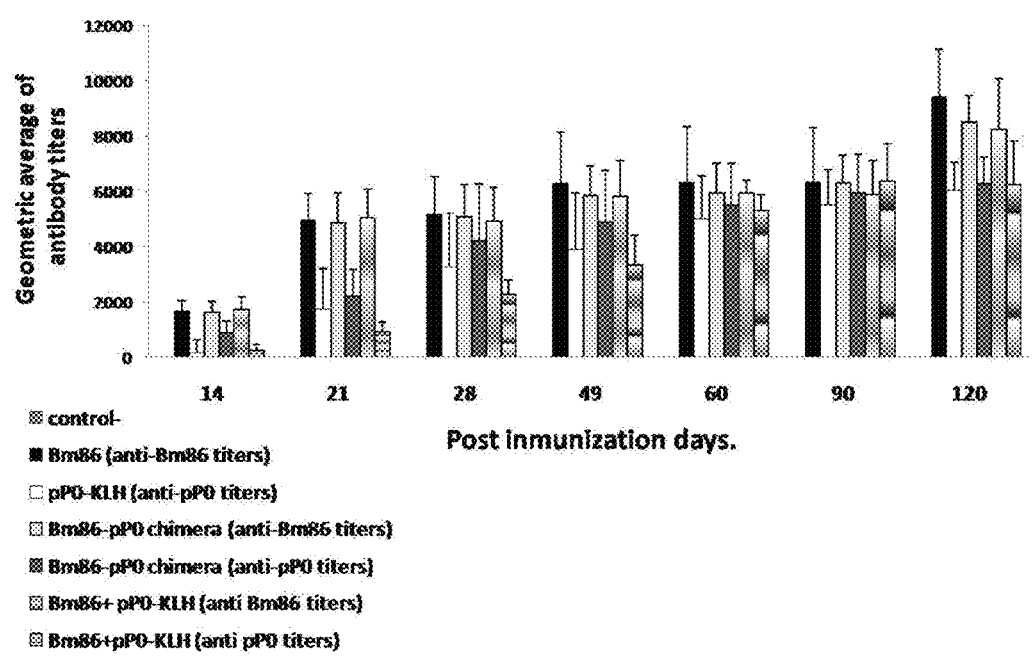

FIG. 10. Anti-peptide P0 and anti-Bm86 IgG antibody response, detected by ELISA in serum from cattle immunized with these antigens individually, combined or with the Bm86-pP0 chimeric protein. Data are expressed as the reciprocal of the antibody titer average, determined as the last serum dilution with an average OD greater than three times the OD average of negative control group. Standard deviations are represented by error bars in the positive direction. No antibody titers were detected for any groups at the beginning of the experiment.

Figure 11:
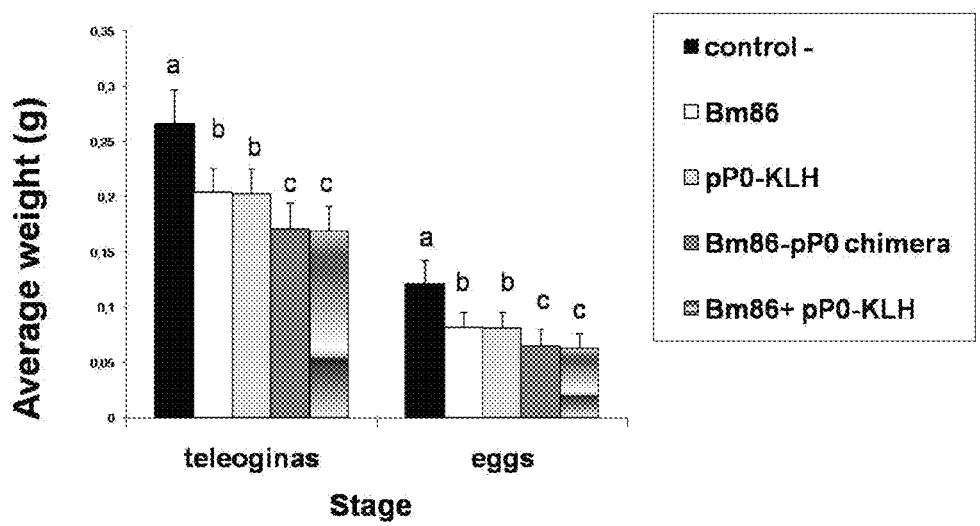

FIG. 11. Average weight of R. microplus aove and teleoginas fed over cattle immunized in the Example 8. The statistically significant differences between experimental groups and each group compared to negative control are represented by different letters (ANOVA and Newman-Keuls multiple comparison test [p<0.05]).

Figure 12:
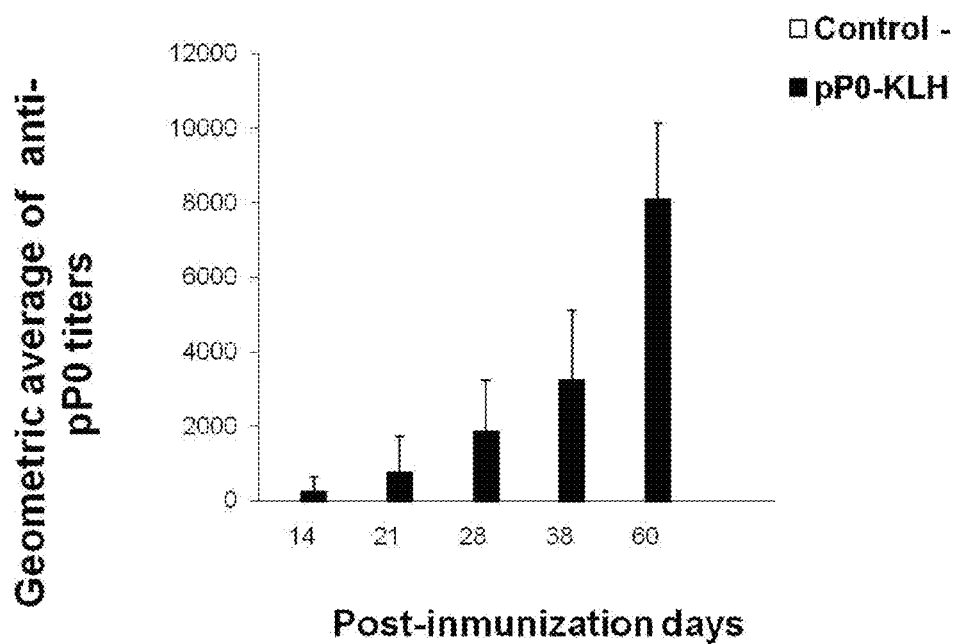

FIG. 12. Anti pP0Is IgG antibodies response detected by ELISA in the serum of rabbits immunized with this antigen and subsequently challenged with I. scapularis. Data are expressed as the reciprocal of the antibody titer average, determined as the last serum dilution with an average OD greater than three times the average OD of negative control group. Standard deviations are represented by error bars in the positive direction. No antibody titers were detected for either group on day zero of the trial.

Figure 13:
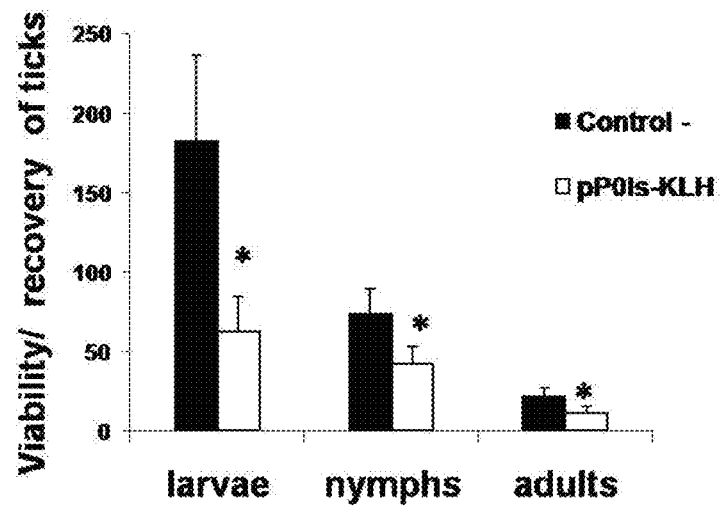
Figure 13:
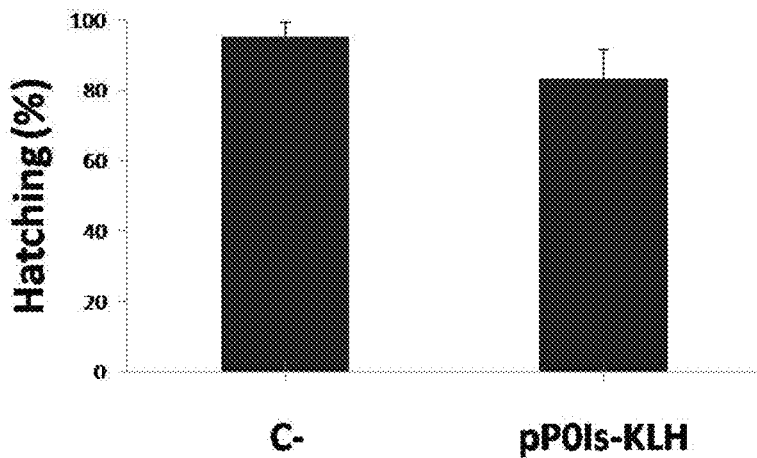

FIG. 13. Behavior of the biological parameters of I. scapularis in rabbits immunized with pP0Is-KLH conjugate. The larvae viability and recovery of nymphs and adult are represented (A) and the percentage of hatching aoves (B). Data are expressed as the mean per group. Standard deviations are represented by error bars in the positive direction. Statistically significant differences with respect to the negative control group are represented by asterisks (ANOVA and Bonferroni multiple comparison test [p<0.05]).

DETAILED DESCRIPTION OF EMBODIMENTS

EXAMPLES

Example 1

Amplification and Cloning of the Nucleotide Sequences Coding for P0 Ribosomal Protein of R. microplus, R. sanguineus and C. rogercresseyi Complementary DNAs (cDNAs) were obtained by reverse-transcription reaction from total RNA of R. microplus and R. sanguineus larvae and C. rogercressey adults. The reactions were carried out following the instructions in the "Reverse Transcription System" kit (Promega, USA # A3500). Nucleotide sequences that encode P0 ribosomal protein of R. microplus and R. sanguineus (SEQ ID No. 1 and SEQ ID No. 2) and P0 sequence of C. rogercresseyi were amplified by Polymerase Chain Reaction (PCR) from the obtained cDNAs. As PCR primers for ticks were used synthetic oligonucleotides designed from the nucleotide sequence reported in Genebank for the P0 protein of *Haemaphysalis longicornis* under the accession number EU048401:

```
                                          (SEQ ID NO: 17)
Forward Oligonucleotide:
5' ATGGTCAGGGAGGACAAGACCACCTGG 3'

(SEQ ID NO: 18)
Reverse Oligonucleotide:
5' CTAGTCGAAGAGTCCGAAGCCCATGTCG 3'
```

As primers for amplification from *C. rogercresseyi* cDNA were used degenerate synthetic oligonucleotides designed from the nucleotide sequences reported in the Genebank for the P0 protein of different ticks species (*Haemaphysalis longicornis* and *Ixodes scapularis*) and insects (*Drosophila melanogaster*, *Culex quinquefasciatus* and *Aedes aegypti*):

```
Forward Oligonucleotides:
F1
5' ATGGGCAAGAACAC(C/G)ATGAT(C/G)ACMC(G/A)GC 3'

F2
5' ATGG(T/G)(T/C)AGGGAG(G/A)ACAA(G/A)(A/G)C (C/A/T)(G/A)C(C/G)TGGAA 3 '

Reverse Oligonucleotide:
R1
5' TC(G/A)AA(A/C/G)AG(G/A/T)C(C/T)GAA(T/G/A)

CCCAT(A/G)TC(A/G)TC 3'
```

As a result of reactions with complementary DNA from ticks obtained a DNA band of approximately 957 bp in both cases, which were cloned into the commercial vector pGEM-Teasy (Promega, USA) for sequencing. For the PCR reaction from complementary DNA of *C. rogercresseyi*, we obtained a DNA band of approximately 780 bp for the combination of primers F1-R1 and a band of approximately 960 bp for the combination of oligonucleotides F2-R1. In both cases the bands were cloned into the commercial vector pGEM-Teasy (Promega, USA) for sequencing.

Example 2

Bioinformatic Analysis

Analysis of amino acid sequence identity were performed using BlastX and ClustalW programs. The deduced 318 amino acid sequences from the amplified DNA sequences of the ticks cDNA were identical between them (SEQ ID NO. 3) and showed a 95% and 93% identity compared to the sequences of P0 ribosomal protein of *Haemaphysalis longicornis* and *Ixodes scapularis* (Genebank, accession number DQ066213), respectively. This sequence also showed 96% identity with the polypeptide sequence deduced from partial reading frame included in the TC533 of the *Amblyoma variegatum* database, and 99% with those deduced from two open reading frames contained in the TC1424 and TC9038, the databases of ESTs from *R. appendiculatus* and *R. microplus*, respectively.

The polypeptide sequence corresponding to the P0 protein of *R. sanguineus* and *R. microplus* referred as SEQ ID NO. 3 also shows a sequence identity of 70% with the bovine P0 (*Bos taurus*, AAX09097 Genebank accession number), being 87% for the last 16 amino acids of the C-terminal region, described as the most immunogenic in the protein. This sequence also shows a sequence identity of 71% with the dog P0 protein (*Canis familiaris*, Genebank accession number XM535894).

In the case of the deduced P0 amino acid sequence from the cDNA sequence of *C. rogercresseyi*, we observed a high identity percentage with the reported sequences for other species of sea lice as *C. clemensi* and *L. salmonis*. As in the case of ticks and their hosts, there was a high sequence identity between the P0 of sea lice with respect to *Salmo salar* P0 (Genebank accession number ACI70184).

The high sequence identity between the P0 of these ectoparasites with respect to host P0 makes it very risky to use this molecules as a vaccine antigen to control their infestations, due to the possibility of generating autoimmunity against the protein of the host. This risk is increased for the use of C-terminal region (last 11-16 amino acids), which is highly conserved among all organisms.

The region of the P0 protein of both species of ticks that has less sequence similarity with mammalian P0 proteins is between amino acids 267 and 301 (SEQ ID NO.4). Using bioinformatics tools, it was found that this region of the protein coincides with an area of low hydrophobicity, which has high chances of being exposed in protein (FIG. 1). Subsequently, we evaluated the immunogenicity of this peptide and its utility as a vaccine antigen to control infestations by these or other species of ticks.

By translating the sequence of the cloned gene that encodes the P0 protein of *Caligus rogercresseyi* sea lice, it was identified a similar peptide with low homology to *Salmo salar* P0 in the same region between amino acids 267 and 301 (SEQ ID NO. 10, pP0Cr). In addition, these were also identified the same regions of lower amino acid similarity (SEQ ID NO. 8 and 9, pP0Cc and pP0Ls) in reported P0 protein for *Caligus clemensi* (Genebank accession number ACO14779) and *Lepeophtheirus salmonis* (Genebank, accession number ACO12290).

Example 3

Synthesis of Peptides and Conjugation to the KLH

The peptides identified as SEQ ID NO. 4, SEQ ID NO. 9 and SEQ ID NO.10, and fragments of 20 amino acids of these peptides were obtained by chemical synthesis and purified by reverse phase chromatography using an HPLC system (High Pressure Liquid Chromatograph). We obtained 15 mg of each synthetic peptide with a purity of 99.3%. The molecular mass of each was verified by mass spectrometry.

In order to enhance the immunogenicity of the peptides were fused to the KLH protein. The conjugations of the synthetic peptides to KLH were performed using the soluble carbodiimide method. The succinic anhydride was used as spacer agent. The separation of the conjugates was performed by gel filtration chromatography. The final concentration of each conjugate was estimated by the bicinchoninic acid method.

Example 4

Obtaining Hyperimmune Mouse Serum Against the Peptide of P0 Ribosomal Protein of *R. microplus* and *R. sanguineus* (pP0)

Six Balb/c, male, 6 weeks old mice with body masses between 18 and 22 g were used in the experiment. They were immunized subcutaneously on days 0, 14, 21 and 28 with 250 µg of pP0-KLH conjugate (equivalent to 125 µg of peptide and 125 µg of KLH) in Freund's adjuvant. Blood draws were performed on days 0, 7, 14, 21, 40 and 65. The animals were bled on day 65 and sera were obtained by centrifugation for 10 minutes at 3500 rpm.

The antibody kinetic was monitored by an indirect ELISA. For the plate coating was used 1 ug per well of pP0 and detection was performed with an anti-mouse IgG conjugated to horseradish peroxidase at 1:15000 dilution. Developing was carried out using a substrate solution containing o-phenylenediamine 0.4 mg/mL in 0.1 M citric acid and 0.2 M $Na_2HPO_4$, pH 5.0 and 0.015% hydrogen peroxide. The reaction was stopped with 2.5 M $H_2SO_4$. The antibody titer was established as the reciprocal of the highest dilution at which mean OD of the serum in question is three times the mean OD of negative control serum.

The immunized animals showed specific antibody titers against the peptide from day 14 of the experiment, which came to be 1:10240 to two of the animals on day 65 (FIG. 2). A mixture containing equal amounts of hyperimmune sera obtained from six immunized mice with the pP0-KLH conjugate was used as a polyclonal antibody in expression and cross-reactivity "in vitro" assays.

Example 5

Expression of the P0 Ribosomal Protein of *Rhipicephalus* Ticks in RK-13 Cell Line and Cross-Reactivity "In Vitro" Assay The DNA sequence that codes for P0 ribosomal protein of *R. sanguineus* (SEQ ID NO.2) was cloned in the plasmid pAdTrack-CMV (9.2 kb), under the control of the immediate/early promoter/enhancer of the human cytomegalovirus (pCMVITh) and late termination/polyadenylation signal of the simian vesicular virus (SV40). This vector contains in its sequence the reporter gene encoding green fluorescent protein (GFP) and the gene conferring kanamycin resistance (He T C et al., Proc Natl Acad Sci U.S.A. 1998, 95: 2509-2514). The resulting plasmid was used to transfect RK-13 cell line of the rabbit kidney. Transfection was performed using lipofectamine (Invitrogen, USA) according to manufacturer's instructions. The transfection efficiency was determined after 24 hours, by observing the GFP expression at the optical microscope using ultraviolet light and a 40× magnification.

Cell lysis was performed after 48 h. Cell extracts were obtained and subjected to electrophoresis on 10% polyacrylamide gel (SDS-PAGE) using reducing and denaturing conditions as described by Laemmli (Laemmli U K, Nature 1970, 227: 680-685).

The expression pattern of P0 ribosomal protein of *Rhipicephalus* ticks was analyzed by Western blotting, using as primary antibody the polyclonal serum against the peptide obtained in mice (diluted 1:3000) and as secondary antibody an anti IgG-mouse conjugated to peroxidase in dilution 1:10000 (FIG. 3). In the sample corresponding to plasmid transfected cells was detected a single band of the expected size for the P0 protein of approximately 35 kDa. The presence of a similar band in the sample run in non-reducing conditions indicated that this peptide is exposed in the three-dimensional protein structure. There was no detectable band in the lane corresponding to the negative control sample (untransfected rabbit RK-13 cells), indicating that the antibodies generated in mice against the 35 amino acids peptide of the P0 protein of *Rhipicephalus* ticks cannot recognize the peptide corresponding to the rabbit P0 protein. It showed the absence of cross-reactivity between tick immunogenic peptide and the peptide corresponding to the rabbit P0 ribosomal protein.

Example 6

Immunogenicity Determination of the pP0 Peptide of *Rhipicephalus* Ticks and their Protective Capacity Against Infestations of *R. sanguineus* Ticks We proceeded to evaluate the usefulness of P0 ribosomal protein peptide of *R. microplus* and *R. sanguineus* as vaccine antigen against the *R. sanguineus* tick. To this end, 20 white New Zealand male rabbits aged between 12 and 14 weeks and body mass of 2.5 kg were randomized into three experimental groups of seven rabbits to groups immunized with Bm86 and pP0-KLH and 6 rabbits for the negative control group immunized with KLH. The immunogens contained in PBS1× were adjuvanted in VG Montanide 888 (prepared to 10% in mineral oil) in a 60/40 proportion of immunogen/adjuvant. The experimental groups were distributed as follows:

Group 1: Subcutaneous immunization with conjugate pP0-KLH at doses of 500 µg/animal (equivalent to 250 mg peptide/animal) on days 0, 21, 36 and 60.

Group 2 (negative control): Subcutaneous immunization with KLH in doses of 250 µg/animal on days 0, 21, 36 and 60.

Group 3 (positive control): Subcutaneous immunization with the *R. microplus* Bm86 protein in doses of 100 µg/animal on days 0 and 28.

The trial lasted 120 days. Serum samples were taken to the animals to measure the antibody response on days 0, 14, 21, 28, 36, 59, 73 and 87. The general behavior and body temperature of the animals were observed daily throughout the test. Three cameras were placed per animal on day 72 of the experiment and each animal was infested on day 73 with approximately 250 larvae, 100 nymphs and 50 adults (20 males and 30 females) of *R. sanguineus* tick. The collection, counting, weighing and molt analyze of ticks was performed between days 75 and 120. The larvae and nymphs collected were kept in an incubator at 28° C. with 80% relative humidity and a photoperiod of 12:12 h (light: dark). The engorged female teleoginas were kept immobilized in individual plastic plates until oviposition in the same conditions.

There was no change in normal behavior, or fever in any of the animals. The humoral response generated against each of the immunogens was assessed by indirect ELISA similar to that described above, coating the plates with 1 µg per well of each antigen. In this case, an IgG anti-rabbit conjugated to peroxidase (SIGMA) was used to develop ELISA in 1:10000 dilutions. The antibody titer mean was determined from individual values in each group. Specific titers against Bm86 were obtained only in animals of group 3 immunized with Bm86. Specific anti-peptide P0 (pP0) titers were obtained only in group 1, which the animals were immunized with pP0-KLH conjugate and specific anti-KLH titers were obtained in groups 1 and 2 immunized with the pP0-KLH conjugate and KLH alone, respectively (FIG. 4).

To study the effect of the immunogens over *R. sanguineus* ticks, the behavior and biological parameters of them were analyzed. The mean feed time and recovery was analyzed in larvae, nymphs and adults. Molting and the capacity of later stage obtained to infesting a virgin animal were also examined in the case of larvae and nymphs. For adults, we studied also the engorged female weight, the egg weight and its hatching rate. The efficiency of conversion to eggs was calculated as described previously (G F Bennett et al.; Acarology 1974, 16: 52-61), the female weight percentage become to eggs. In general, larvae, nymphs and adults fed over Bm86 immunized rabbits took longer time to eat than the same stages fed over the control and vaccinated with the P0 peptide animals. The recovery of larvae, nymphs and adults among groups was compared by ANOVA and Bonferroni multiple comparisons test (p<0.01). In the cases of larvae and nymphs, survival or viability was analyzed as the final amount of the next stage that was able to infect naive animals with respect the number of larvae and nymphs molted. For adults, viability was measured as the final number of ticks capable of surviving after incubation with the capacity to lay eggs. The mean recovery of larvae showed no statistically significant differences between the experimental groups. In the case of nymphs recovery, despite a tendency to recover less nymphs fed on the groups immunized with both pP0-KLH and Bm86 than nymphs fed over the control group immunized with KLH, there were no statistically significant differences. In the case of adults, recovery showed statistically significant differences for the group vaccinated with the antigen pP0 relative to negative control and vaccinated with Bm86 groups (FIG. 5).

There were serious effects on the viability and appearance of newly molted nymphs from larvae fed in groups vaccinated with both antigens (pP0-KLH and Bm86) compared to the control group collected. The group vaccinated with the pP0-KLH showed a high mortality of newly molted nymphs with a clear involvement of the morphology. Statistically significant differences were found in the viability between groups vaccinated with the PP0-KLH and Bm86 compared to negative control group. There are also significant differences in viability between the group vaccinated with Bm86 and the group vaccinated with pP0-KLH (FIG. 6). Table 1 shows the mortality percentages in each experimental group.

TABLE 1

Mortality Percentages of newly molted nymphs from larvae fed over the three experimental groups.

| Stages | Mortality (%) |
| --- | --- |
| pP0-KLH | 77.70 $^b$ |
| KLH | 13.45 $^a$ |
| Bm86 | 44.70 $^c$ |

Different letters mean statistically significant differences obtained by ANOVA followed by Bonferroni multiple comparison test (P < 0.001) of the transformed data.

The ability of newly molted nymphs and adults and newly hatched larvae from experimental groups to infect a new animal was determined by the infestation of virgin dogs with recovered, molted and viable specimens for each experimental group. No statistically significant differences were found for this parameter between the experimental groups.

Statistical analysis of teleogina and egg weight data was performed using ANOVA and Bonferroni multiple comparison test (p<0.05). No significant differences were found for both parameters between experimental groups. The efficiency of conversion to eggs was not significantly different between the vaccinated groups and control group. At this point, we note that 10% of adults fed on rabbits immunized with pP0-KLH did not lay eggs; about 3% in the control group immunized with KLH and 6% did not lay eggs in the group fed on rabbits immunized with Bm86. There were statistically significant differences (p<0.01) in % of eggs hatched in the group immunized with pP0-KLH respect to the control group immunized with KLH (FIG. 7). Although the eggs lay by teleoginas fed on the group immunized with Bm86 were hatching a percent lower than in the negative control group, these differences were not significant from a statistical point of view. Larvae hatched from the eggs of the three experimental groups were able to infest dogs and eat normally.

Experiments were conducted with results similar to those previously described in this example, immunizing rabbits with fragments of 20 amino acids of the pP0. The peptides tested have the following amino acid sequences: AAGGGAAAAKPEESKKEEAK (SEQ ID NO: 11) EYLKDPSKFAAAAAPAAGGG (SEQ ID NO: 13) and FAAAAAPAAGGGAAAAKPEE (SEQ ID NO: 12). These peptides were conjugated to KLH. The best results were obtained with the peptide corresponding to the last 20 amino acids of the pP0.

Example 7

Immunogenicity determination of R. microplus and R. sanguineus pP0 Fused to Different Immunopotentiator Molecules The VP60 capsid protein of RHDV (strain AST/89) was obtained with high expression levels in the rupture supernatant of the *Pichia pastoris* yeast. This protein generated by recombinant techniques forms high molecular weight multimers with antigenic and structural features similar to the native viral particle (Farnós O. et al.; AntiVir. Res 2009, 81: 25-36). Taking advantage of the high immunogenicity of these virus-like particles (VLPs), a recombinant DNA construct for the pP0 exposed on the surface of the RHDV VLPs was generated. To this end, the nucleotide sequence encoding the 20 aa fragment from position 15 to 35 of the SEQ ID No.4 of this peptide (AAGGGAAAAKPEESKKEEAK) was inserted into the pNAOVP60 plasmid in the protruding domain position of VP60 protein gene. This construction allows the pP0 is expressed fused to the C-terminus of VP60, a region that is exposed to the outside after the assembly of VLPs. The recombinant plasmid obtained was used to transform the MP36 strain of *P. pastoris*. The VP60pP0 protein was obtained soluble in the breaking supernatant at levels of 350 mg/L. Exposure of the C-terminal region and the formation of VLPs were verified by a sandwich ELISA using an anti-RHDV hyperimmune sera and 6H6 and 1H8 monoclonal antibodies (kindly donated by Dr. Lorenzo Capucci Istituto Zooprofilattico Sperimentale della Lombardia, Brescia, Italy) which recognize epitopes present in the VP60 protein C-terminus and viral particles or VLPs assembled correctly (L. Capucci et al.; Virus. Res 1995, 37: 221-238). VP60pP0 VLPs were purified by HPLC on a TSK-G3000PW, obtaining a purity of approximately 50%.

The other recombinant construction was carried out with the same peptide of 20 aa P0 coupled to several promiscuous T cell epitopes. Specifically, we used tetanus toxoid ttP2 epitopes and T cell epitope of measles virus (TT-MVF). Multiple copies of the DNA sequence of 20 aa pP0 (AAGGGAAAAKPEESKKEEAK) (SEQ ID NO: 11) and promiscuous T antigen were inserted fused to the intein of *Saccharomyces cerevisiae* in the plasmid pTBY 12 under control of the T7 promoter and lac operon repressor that allows expression of the fusion protein only after induction with IPTG. The recombinant plasmid obtained was used to transform ER2566 *E. coli* strain. The TT-MVF-pP0-intein chimera peptide was detected in the breaking supernatant of this strain by the anti-pP0 mouse polyclonal serum. Expression levels were estimated at approximately 100 mg/L of culture. The peptide was purified by affinity on a column of chitin and auto-digested in the presence of thiol groups to release the peptide of interest.

An immunization experiment was conducted in rabbits to assess the immunogenicity of chimera variants obtained and the effects of these antibodies generated on the R. sanguineus larvae, nymphs and adults compared to the effect of the synthetic peptide of P0 ribosomal protein conjugated to hemocyanin. For this experiment, 28 New Zealand rabbits, white and male, were randomized into 4 groups of 7 animals each. The immunogens were adjuvanted in Montanide VG 888 and administered as follows:

Group 1: Subcutaneous immunization with pP0-KLH conjugate at doses of 500 µg/animal (equivalent to 250 µg peptide/animal).
Group 2 (negative control): Subcutaneous immunization with KLH in doses of 250 µg/animal.
Group 3: Subcutaneous immunization with VLPsVP60pP0 in doses of 250 µg protein/animal.
Group 4: Subcutaneous immunization with the TT-MVF-pP0 chimeric peptide in doses of 250 µg peptide/animal.

The trial lasted 90 days. Animals were immunized on days 0, 21 and 36. The sera extraction, the antibody titer determinations, tick infestation and collection were performed similarly as described in Example 6.

For statistical analysis, the recovery and viability of ticks were subjected to analysis of variance (ANOVA) and a Bonferroni multiple comparison test. The best anti-P0 peptide titers were detected in animals immunized with the chimera VLPsVP60pP0 from day 14 post-immunization. These antibody titers were higher than 1:5000 for VLPsVP60pP0 chimeric from day 21, and from day 28 for animals immunized with the TT-MVF-PP0 chimera. These titers were kept until the end of the experiment (FIG. 8 A).

The mean viability of larvae and nymphs and the adult recovery showed significant differences ($p<0.05$) for the groups vaccinated with chimera P0 peptide variants with respect to the negative control group immunized with KLH. (FIG. 8 B). Table 2 shows the diminution in the percentage of viability of larvae and the recovery percentage of nymphs and adults by experimental groups respect to the negative control group.

TABLE 2

Diminishing in the recovery percentage of ticks in each stage with respect to the control group immunized with KLH.

| Stage | pP0-KLH (%) | TT-MVF-pP0 (%) | VLPsVP60pP0 (%) |
|---|---|---|---|
| Larvae | 30.00 | 28.00 | 34.00 |
| Nymphs | 38.00 | 16.00 | 42.00 |
| Adults | 36.67 | 30.00 | 36.67 |

Example 8

Protective Capacity Determination of the Bm86-pP0 Chimera Protein Respect to the pP0, Against R. microplus Tick Infestations The Bm86 antigen from the R. microplus tick was expressed earlier in the MP36 P. pastoris strain (Valle M R et al., J. Biotech. 1994, 33: 135-146). In this construction were removed Bm86 gene fragments as the signal peptide and transmembrane region of the protein (SEQ ID NO. 5). To construct the chimera Bm86-pP0 protein, the nucleotide sequence of the Bm86 protein described above was inserted next the secretion signal of S. cerevisiae sucrose invertase (ssSUC2) in pPS10 plasmid under the control of AOX 1 promoter. The DNA sequence encoding the 35 amino acids peptide of R. microplus P0 ribosomal protein was fused to this Bm86 sequence. The MP36 P. pastoris strain was transformed with the resulting plasmid and transformants were selected by the reversal of the amino acid histidine auxotrophy. The clones obtained were induced with methanol after reaching an OD between 3 and 4 in cell culture. After 96 hours of induction, an expression analysis was carried out by Western blotting using the anti-pP0 mouse hyperimmune serum (referred in Example 4) and an anti-Bm86 polyclonal serum (FIGS. 9A and 9B). The recombinant protein was detected in the cell disruption precipitate at levels of 300 mg/L. This analysis showed a band of 100 kDa, corresponding to the glycosylated protein, which was reduced to a band of approximately 70 kDa, coinciding with the expected size for the protein after digestion with the PNGase F enzyme. There was no band in the sample analyzed in non-reducing conditions, suggesting the formation of multimeric structures, which were unable to enter the polyacrylamide gel. The presence of these protein aggregates of high molecular weight in the rupture precipitate was verified by electron microscopy. The chimera protein was purified by acid precipitation method, obtaining a purity of about 95%.

A cattle immunization test was conducted to compare the effects of pP0-KLH conjugate, Bm86 protein, Bm86-pP0 chimera protein and co-administration of pP0-KLH and Bm86 antigens as vaccine candidates on R. microplus ticks. For this experiment, 20 cattle free of ticks, more than 240 kg were randomized into five experimental groups of 4 animals each. The immunogens were administered in Montanide 888 VG (prepared to 10% in mineral oil) in 60/40 ratio of aqueous phase/oil phase. The experimental groups were designed as follows:

Group 1: Intramuscular immunization with pP0-KLH conjugate in doses of 500 µg of conjugate/animal (equivalent to 250 µg peptide/animal) with the scheme of 0, 4 and 7 weeks.
Group 2 (negative control): Intramuscular immunization with KLH in doses of 250 µg/animal with the scheme of 0, 4 and 7 weeks.
Group 3 (positive control): Intramuscular immunization with the R. microplus Bm86 protein in doses of 250 µg/animal with the scheme of 0, 4 and 7 weeks.
Group 4: Intramuscular immunization with the pP0-Bm86 chimeric protein in doses of 250 µg/animal with the scheme of 0, 4 and 7 weeks
Group 5: Intramuscular immunization with Bm86 protein and pP0-KLH conjugate in a dose of 250 mg of Bm86/animal and 500 µg of conjugate/animal with the scheme of 0, 4 and 7 weeks.

The trial lasted a total of 140 days. The animal serum samples were taken to measure the antibody response on days 0, 14, 28, 49, 70, 82, 120 and 140. Four cameras were placed per animal at day 82 of the experiment and were infested with 3000 larvae per chamber (12000 larvae per animal) of R. microplus ticks at a rate of 4000 daily between days 84 and 86. The collection, counting and weighing of ticks was performed between days 107 and 117. The engorged female teleoginas were kept in individual plastic plates at 28° C., 90% of relative humidity and a photoperiod of 12:12 h (light: dark).

The kinetic of anti-Bm86 and anti-pP0 antibodies was studied by ELISA, using in this case an anti-bovine conjugated peroxidase (Sigma) at 1:10000 dilutions. A specific IgG antibody response against Bm86 and against pP0 from day 14 was detected in all animals immunized with these antigens. These antibody titers were higher than 1:5000 after day 28 for the Bm86 antigen and between days 60 and 90 for the case of P0 peptide, which remained until the end of the experiment.

No statistically significant differences were found for the titles of anti-Bm86 or anti-PP0 antibodies between groups inoculated with both antigens separately or in combination, or with respect to the group vaccinated with Bm86-pP0 chimera (FIG. 10).

The effect of the antibodies generated in this experiment over the teleogina recovery, the teleogina and egg weight and hatching rate of *R. microplus* ticks was analyzed. Teleogina recovery significantly decreased in all vaccinated groups compared to negative control group of the experiment. The recovery of ticks respect the negative control group was decreased 32.6% for the group immunized with Bm86, 55.2% for the group immunized with pP0-KLH conjugate, 62.13% for the group immunized with two individual antigens and 65.2% for the immunization with Bm86-pP0 chimera. This parameter was significantly lower for the groups immunized with the Bm86-pP0 chimera and the combination of Bm86 with pP0-KLH respect to the groups where these antigens were applied individually. There were no significant differences in the group immunized with the chimera compared to the group immunized with the combination of the two antigens. The parameters of teleogina and eggs weight showed a significant affectation in the groups immunized with Bm86 relative to negative control group (ANOVA and Newman-Keuls multiple comparison test [p<0.05]). A significant decrease was observed for these biological parameters in the groups immunized with the chimera Bm86-pP0 and the combination of antigens, compared to groups vaccinated with the individual antigens (FIG. 11). The percentage of hatching in the negative control group was 87.4%, while for the groups immunized with Bm86, pP0-KLH, the combination of Bm86 and pP0-KLH and Bm86-pP0 chimera was 75.1%, 64.6%, 54.8% and 55.9% respectively, showing a significant decrease in all groups compared to control. These results show that vaccination with a formulation containing the peptide of P0 ribosomal protein, object of this invention, fused to the protein Bm86 or combined with it leads to increased affectations on survival and biological parameters of *R. microplus*, which results in a more efficient control of infestations of this tick.

Example 9

Protective Capacity Determination of the P0 Peptide of *Ixodes scapularis* (pP0Is) Against *I. scapularis* Tick Infestations The immunogenicity of the peptide between amino acids 267-302 of *I. scapularis* P0 ribosomal protein, homologous to the immunogenic peptide of the *R. microplus* and *R. sanguineus* P0 protein was evaluated. These peptides have a 68% of sequence identity among them. The chemical synthesis of *I. scapularis* peptide and conjugation to hemocyanin (KLH) was performed similarly as described in Example 3. Subsequently, 12 white New Zealand male rabbits were randomized into two experimental groups of six rabbits each, which were immunized and challenged with larvae, nymphs and adults of *I. scapularis* ticks. The immunogens were adjuvanted with Montanide 888 VG in a ratio 60/40 of immunogen/adjuvant and applied as follows:
Group 1: Subcutaneous immunization with pP0Is-KLH conjugate at doses of 500 µg/animal (equivalent to 250 µg peptide/animal).
Group 2 (negative control): Subcutaneous immunization with KLH in doses of 250 µg/animal.

Both groups were immunized on days 0, 21 and 36. Sera extractions were performed at days 0, 14, 21, 28, 36 and 60 of the experiment. The determination of anti-pP0Is antibody titers and infestation, collect, count and maintenance of ticks were performed similarly as described in Example 6.

There was no change in normal behavior, neither fever in any of the animals. Anti-pP0Is titers were detected in animals immunized with pP0Is-KLH conjugate from day 14 post-immunization. These antibody titers were higher than 1:3500 on day 36, which remained until the end of the experiment (FIG. 12).

At 168 hours, all fed stages of the two groups had been collected. Recovery and viability of all stages of ticks, the weight of teleoginas and eggs and egg hatch % were compared between groups by ANOVA and Bonferroni multiple comparison test (p<0.05). The recovery of nymphs and teleoginas showed statistically significant differences in the group vaccinated with the pP0Is-KLH conjugate compared to negative control group. A high mortality of newly molted larvae fed over pP0Is-KLH immunized animals was found with statistically significant differences between groups (FIG. 13 A). The weight of teleoginas and eggs was not shown statistically significant differences. The efficiency of conversion to eggs was 45.49% in the negative control group and 40.19% in the group immunized with the pP0Is-KLH conjugate. The percentage of hatching was 95.20% for negative control and 83.10% for the group immunized with the conjugate. This last parameter was significant when statistical analysis was performed (FIG. 13 B).

Example 10

Protective Capacity Determination of the *L. salmonis* pP0 (pP0Ls)

To evaluate the usefulness of the pP0Ls as vaccine antigen, 80 salmon with an average weight of 80 g were distributed in 4 groups of 20 fish each. Two groups were injected intraperitoneally (ip) with pP0Ls-KLH conjugate at a dose of 10 µg conjugate/g body weight of salmon (equivalent to 5 µg pP0Ls/g salmon), formulated in Montanide 888 oil adjuvant. The other two negative control groups were immunized with KLH 5 µg/g body weight, adjuvanted in Montanide 888. After 500 arbitrary thermal units, the salmons were adapted to seawater and were infested with 2000±200 copepodites per pond. The challenge was carried out under dark conditions, constant aeration, support oxygenation, temperature (15-17° C.) and salinity (approx. 30 ppm) control. In order to avoid loss of copepodites and facilitate their attachment, the flow of water in the pond was closed and the replacement was done manually every 48 hours. In addition, 220µ sieves were installed in the sewer. The instant of the inclusion of copepodites was defined as day 0. These conditions were maintained for 40 days from the start of the challenge.

At day 40, the fishes were sacrificed by an anesthesia overdose, and the evaluation of the results proceeded by parasites counting. The results in the Table 3 showed a significant decrease in the number of parasites per fish in the groups vaccinated with pP0Ls-KLH, compared to negative controls immunized with KLH alone.

TABLE 3

Parasite count results at the end of the challenging experiment.

| Parameters | Vaccinated group 1 | Vaccinated group 2 | Control 1 | Control 2 |
|---|---|---|---|---|
| # of parasites/fish | 15 ± 6$^a$ | 16 ± 6$^a$ | 38 ± 9$^b$ | 37 ± 10$^b$ |
| % of fish survival | 95 | 90 | 95 | 85 |
| % Infestation inhibition | 60 | 56 | — | — |

Different letters indicate significant differences. Dunn multiple comparison test was applied (p<0.001).

Salmon immunization experiments with 20 amino acid fragments of pP0Ls peptide were performed with similar results to those described in this example. The peptides with the sequence PAAGATKAAAAAPAKADEPE (SEQ ID NO: 14), SKFASVAAAPAAGATKAAAA (SEQ ID NO: 15) and EYLADPSKFASVAAAPAAGA (SEQ ID NO: 16) were tested conjugated to KLH. Although all peptides conferred protection, the best results were obtained with the peptide corresponding to the last 20 amino acids of pP0Ls.

Example 11

Protective Capacity Determination of the P0 Peptide of *C. Rogercresseyi* (pP0Cr) Fused to Promiscuous T Epitopes and Conjugated to KLH (pP0Cr-KLH)

Example 11

Protective Capacity Determination of the P0 Peptide of *C. rogercresseyi* (pP0Cr) Fused to Promiscuous T Epitopes and Conjugated to KLH (pP0Cr-KLH)

We assessed the immunogenicity of the pP0Cr-KLH conjugate and the pP0Cr fused to other immuno-carrier molecules such as promiscuous T epitopes. In this case, ttP2 epitopes of tetanus toxoid and T cell epitope of measles virus (TT-MVF) were used. The TT-MVF-pP0Cr chimera peptide was detected in the supernatant culture of MP36 *P. pastoris* strain transformed with a plasmid containing a copy of the coding sequence for pP0Cr fused at its N-terminus to two copies of the promiscuous T epitopes under the control of the promoter of alcohol oxidase 1 (AOX 1). All was preceded by the secretion signal of *S. cerevisiae* sucrose invertase (ss-SUC2). Expression levels were estimated at approximately 150 mg/L of culture.

The usefulness of this polypeptide obtained by recombinant means was evaluated as vaccine antigen and compared with the effects of pP0Cr-KLH conjugate. 120 salmons with an average weight of 80 g were divided into 6 groups of 20 fish each. The experimental groups were:
Groups 1 and 2 were injected i.p. with the pP0Cr-KLH conjugate at a dose of 10 µg/g body weight (equivalent to 5 µg pP0Cr/g).
Groups 3 and 4 were injected i.p. with KLH at a dose of 5 µg/g weight.
Groups 5 and 6 were injected i.p with the TT-MVF-pP0Cr. chimera protein at a dose of 5 µg/g weight.

In all cases, the immunogen was formulated in Montanide 888 oil adjuvant. The experimental procedure was similar to Example 10, except that in this case as *C. rogercresseyi* sea lice has a shorter life cycle, on day 24 (after complete two life cycles of the parasite), fishes were sacrificed with an overdose of anesthesia, and the evaluation of the results proceeded by parasites counting. The following table shows a significant decrease in the number of parasites per fish in the groups vaccinated with pP0Cr-KLH and TT-MVF-pP0Cr, compared to negative controls immunized with KLH alone. The best protection, assessed as number of parasites/fish was observed in the group TT-MVF-pP0Cr.

TABLE 4

Parasite count results at the end of the challenging experiment.

| Parameters | Group 1 | Group 2 | Group 3 | Group 4 | Group 5 | Group 6 |
|---|---|---|---|---|---|---|
| # parasites/fish | $21 \pm 7^a$ | $19 \pm 6^a$ | $48 \pm 10^b$ | $47 \pm 8^b$ | $14 \pm 3^c$ | $13 \pm 2^c$ |
| % fish survival | 90 | 85 | 95 | 85 | 95 | 90 |
| % infestation inhibition | 55 | 60 | — | — | 70 | 72 |

Different letters indicate significant differences. Dunn multiple comparison test was applied (p<0.001).

Example 12

Immunogenicity Determination of the pP0Cr Fused to My32 Polypeptide

A my32-pP0Cr chimera peptide using the same procedure described in the above examples for all fusion proteins was generated to evaluate the immunogenicity of the pP0Cr antigen fused to my32, previously known. In this case, the plasmid that was used to transform the *P. pastoris* MP36 strain contained a copy of pP0Cr fused by its N-terminus to a copy of my32 protein, under the control of the AOX 1 promoter, preceded by the ssSUC2 secretion signal. The my32-pP0Cr chimera peptide was detected in the culture supernatant at a concentration of approximately 135 mg/L of culture.

To evaluate the usefulness of this polypeptide obtained by recombinant via as vaccine antigen, 160 salmons with an average weight of 80 g were divided into groups of 20 fish each. The experimental groups were:
Groups 1 and 2 were injected with the pP0Cr-KLH conjugate at a dose of 10 µg/g body weight (equivalent to 5 µg pP0Cr/g).
Groups 3 and 4 were injected with KLH at a dose of 5 µg/g body weight.
Groups 5 and 6 were injected with pP0Cr-my32 chimera protein at a dose of 5 µg/g body weight.
Groups 7 and 8 were injected with the my32 protein obtained by recombinant means, at a dose of 5 µg/g body weight.

All animals received the immunogen by the ip route adjuvanted in Montanide 888. The experimental procedure followed was similar to that of Example 11. Table 5 shows the results of sampling at day 24 post-challenge, which evidenced a significant decrease in the number of parasites per fish in the groups vaccinated with pP0Cr-KLH, my32-pP0Cr, and my32 compared with animals inoculated only with KLH. The best protection, assessed as number of parasites/fish was observed in group pP0Cr-my32.

TABLE 5

Parasite count results at the end of the challenging experiment.

| Parameter | Group 1 | Group 2 | Group 3 | Group 4 | Group 5 | Group 6 | Group 7 | Group 8 |
|---|---|---|---|---|---|---|---|---|
| # parasites/fish | $17 \pm 7^a$ | $15 \pm 6^a$ | $30 \pm 9^b$ | $31 \pm 8^b$ | $3 \pm 1^c$ | $4 \pm 2^c$ | $15 \pm 3^a$ | $14 \pm 6^a$ |
| % fish survival | 85 | 95 | 95 | 85 | 90 | 95 | 95 | 85 |

TABLE 5-continued

Parasite count results at the end of the challenging experiment.

| Parameter | Group 1 | Group 2 | Group 3 | Group 4 | Group 5 | Group 6 | Group 7 | Group 8 |
|---|---|---|---|---|---|---|---|---|
| % infestation inhibition | 43 | 50 | — | — | 90 | 87 | 50 | 53 |

Different letters indicate significant differences. We applied a Dunn multiple comparison test (p<0.001).

INCORPORATION OF SEQUENCE LISTING

Incorporated herein by reference in its entirety is the Sequence Listing for the application. The Sequence Listing is disclosed on a computer-readable ASCII text file titled, "sequence_listing.txt", created on Apr. 28, 2014. The sequence_listing.txt file is 15.4 kb in size.

The invention claimed is:

1. An immunogenic composition for controlling infestation by ectoparasites, said composition comprises an isolated peptide consisting of amino acids of the region between 267 and 301 of the P0 ribosomal protein of said ectoparasites wherein said peptide is selected from the group consisting of SEQ ID NO. 4, SEQ ID NO. 6, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, and a peptide that exhibits at least 85% identity with such sequences consisting of SEQ ID NO. 4, SEQ ID NO. 6, SEQ ID NO. 8, SEQ ID NO. 9, or SEQ ID NO. 10; wherein said isolated peptide has been fused or conjugated with another molecule to increase their immunogenicity or enhance their protective effect.

2. The composition of claim 1, wherein said molecule is selected from the group consisting of hemocyanin, a T cell epitope from tetanus toxin or fusion protein of measles virus, proteins that form virus-like particles of Rabbit Hemorrhagic Disease Virus, the Bm86 protein from the *R. microplus* tick, the Rs86 protein from the *R. sanguineus* tick and my32 protein of *C. rogercresseyi* or *L. salmonis* sea lice.

3. The composition of claim 1, wherein said-peptide is obtained by DNA recombinant techniques or chemical synthesis.

4. The composition according to claim 3, wherein said peptide is obtained by expression in yeast, bacteria, plants, insect larvae, insect or mammalian cells.

5. The composition according to claim 1, wherein said composition further comprises a vaccine adjuvant.

6. An immunogenic composition for controlling infestations by ectoparasites, said composition is comprises a nucleic acid sequence encoding a peptide consisting of amino acids of the region between 267 and 301 of the P0 ribosomal protein of said ectoparasites wherein said peptide is selected from the group consisting of SEQ ID NO. 4, SEQ ID NO. 6, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, and SEQ ID NO: 16 wherein said isolated nucleic acid has been fused or conjugated with another molecule to increase their immunogenicity or enhance their protective effect.

7. A method for controlling ectoparasite infestations, said method comprising administration of a composition comprising naked nucleic acids encoding a polypeptide of the P0 ribosomal protein of said ectoparasites, said polypeptides selected from the group consisting of SEQ ID NO. 4, SEQ ID NO. 6, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16 and any polypeptide that exhibits at least 85% identity with such sequences consisting of SEQ ID NO: 4, SEQ ID NO: 6, SEQ ID NO: 8, SEQ ID NO: 9 or SEQ ID NO: 10; wherein said isolated nucleic acid has been fused or conjugated with another molecule to increase their immunogenicity or enhance their protective effect.

8. A method for controlling infestation by ectoparasites, said method comprises administering a composition according to claim 1.

9. A method according to claim 8, wherein said ectoparasites are ticks, sea lice, or pathogens transmitted with said ectoparasites.

10. The method of 8, wherein said method comprises administration of said peptide by injection, in the range of 0.001 to 25 µg peptide/g weight of the animal vaccinated, using feed formulations in a range of 0.01 to 300 µg peptide/g of feed or by immersion baths for fish in the range of 0.01-10 mg peptide/L of water.

\* \* \* \* \*

UNITED STATES PATENT AND TRADEMARK OFFICE
CERTIFICATE OF CORRECTION

PATENT NO. : 9,085,634 B2
APPLICATION NO. : 13/825892
DATED : July 21, 2015
INVENTOR(S) : Rodriguez Mallon et al.

It is certified that error appears in the above-identified patent and that said Letters Patent is hereby corrected as shown below:

In the Specification

Column 1, line 62,
now reads: "other currently constitutes"
should read: -- others currently constitute --

Column 2, line 54,
now reads: "whichs form"
should read: -- which form --

Column 3, line 30,
now reads: "p0ribosomal"
should read: -- p0 ribosomal --

Column 7, line 40,
now reads: "according the case"
should read: -- according to the case --

Signed and Sealed this
Twenty-sixth Day of April, 2016

Michelle K. Lee
*Director of the United States Patent and Trademark Office*

CERTIFICATE OF CORRECTION (continued)
U.S. Pat. No. 9,085,634 B2

In the Specification

Column 9, lines 18-28, now reads: "F1 . . . 3'"

"F2 . . . 3'"

"F3 . . . 3'"

should read: -- F1 . . . 3' (SEQ ID NO: 19) --

-- F2 . . . 3' (SEQ ID NO: 20) --

-- F3 . . . 3' (SEQ ID NO: 21) --

```
SEQUENCE LISTING

<160> NUMBER OF SEQ ID NOS: 21

<210> SEQ ID NO 1
<211> LENGTH: 957
<212> TYPE: DNA
<213> ORGANISM: Rhipicephalus microplus

<400> SEQUENCE: 1
atggtcaggg aggataagac gacctggaag agcaactact tcctgcgact ggtgcagctg    60
ctcgacgagt accccaagtg cttcatcgtg ggtgtagaca atgtcggctc gaagcagatg   120
cagacgatcc gtgtttcgct ccgcaagcac gccgtcctgc tcatgggcaa gaacaccatg   180
atccgcaagg ccatccgcgg acacctggac aacaacccgg ccctggagaa gctgttgccg   240
cacatcaagg gcaacgtcgg tttcgttttc accaaggaag acctgactga ggtgcgcgag   300
aagatcatcg acaacaaggt gaaggcgcct gcccgtgctg gtgccctcgc cccctggat   360 gtcatgatcc cggctcagaa cactggcctc ggccccgaga agacctcttt cttccaggcc   420
ctgcagattc ccaccaagat ctcaaagggt actattgaaa ttctcaacga gatccatttg   480
atcaagaagg atgaccgtgt cggtgcttcc gaggctacgc ttctaaacat gttgaacatc   540
tcgcccttct catatggtct gaagatcctg caggtgtacg actcgggtac tgtcttctcc   600
cctgacatct tggacatcac accagaggac ctgcgatcag cgtttgttga gggtgtccgc   660
aatgttgctg ccgtatcctt gtccatcgga tacccgactg ttgcatcagt cccacactcc   720
attgtcaatg gtctcaagaa cctcattgcc attgctgtgg agaccgacat tacattcaag   780
gaggctgaaa tggccaagga gtacctcaag gacccgtcga agttcgctgc agcagcagct   840
ccagccgcag ggggtggggc agctgcagcc aagccggagg agtcgaagaa ggaagaagcc   900
aagaaggagg aatccgaaga ggaggacgac gatatgggct tcggactctt cgactag    957

<210> SEQ ID NO 2
<211> LENGTH: 957
<212> TYPE: DNA
<213> ORGANISM: Rhipicephalus sanguineus

<400> SEQUENCE: 2
atggtcaggg aggataagac gacctggaag agcaactact tcctgcggct ggtgcagctg    60
ctcgacgagt accccaagtg cttcatcgtg ggcgtcgaca atgtcggttc gaagcagatg   120
cagacgatcc gtgtttcgct ccgcaagcac gccgtcctgc tcatgggcaa gaacaccatg   180
```

```
atccgcaagg ccattcgcgg acacctggac aacaacccgg ccctggaaaa gctgttgcca    240
cacatcaagg gcaacgtcgg tttcgtcttc accaaggaag acctgacaga ggtgcgtgag    300
aagatcattg acaacaaggt gaaggcgcct gcccgtgccg gtgccctggc ccctctggac    360
gtcatgatcc cggcgcagaa caccggcctc ggtcccgaga agacctcttt cttccaggcc    420
ctgcagatcc ccaccaagat ctcgaagggt accattgaaa ttctcaatga gatccacttg    480
atcaagaagg acgacagggt gggcgcttcc gaggccacgc ttctcaacat gttgaacatc    540
tcgcccttct cgtatggtct gaagattctg caggtgtacg actccggtac cgtgttctcc    600
cctgacattt tggacatcac accagaggac ttgagatcag cattcgtcga gggtgtccgc    660
aatgtcgctg ctgtatcctt gtccatcgga tacccgactg ttgcatcagt cccacactcc    720
attgtcaacg gtctcaagaa cctcattgcc attgccgtgg agacagacat cacgttcaag    780
gaggctgaaa tggccaagga gtacctcaag gacccgtcga agttcgctgc agcagcagct    840
ccagccgcag gaggtggggc agccgcagcc aagccggagg agtcgaagaa ggaagaagct    900
aagaaggagg aatccgaaga ggaggacgac gatatgggct tcggactctt cgactag      957
```

<210> SEQ ID NO 3
<211> LENGTH: 318
<212> TYPE: PRT
<213> ORGANISM: Rhipicephalus microplus

<400> SEQUENCE: 3

Met Val Arg Glu Asp Lys Thr Thr Trp Lys Ser Asn Tyr Phe Leu Arg
1               5                   10                  15

Leu Val Gln Leu Leu Asp Glu Tyr Pro Lys Cys Phe Ile Val Gly Val
            20                  25                  30

Asp Asn Val Gly Ser Lys Gln Met Gln Thr Ile Arg Val Ser Leu Arg
        35                  40                  45

Lys His Ala Val Leu Leu Met Gly Lys Asn Thr Met Ile Arg Lys Ala
    50                  55                  60

Ile Arg Gly His Leu Asp Asn Asn Pro Ala Leu Glu Lys Leu Leu Pro
65                  70                  75                  80

His Ile Lys Gly Asn Val Gly Phe Val Phe Thr Lys Glu Asp Leu Thr
                85                  90                  95

Glu Val Arg Glu Lys Ile Ile Asp Asn Lys Val Lys Ala Pro Ala Arg
            100                 105                 110

Ala Gly Ala Leu Ala Pro Leu Asp Val Met Ile Pro Ala Gln Asn Thr
        115                 120                 125

Gly Leu Gly Pro Glu Lys Thr Ser Phe Phe Gln Ala Leu Gln Ile Pro
    130                 135                 140

Thr Lys Ile Ser Lys Gly Thr Ile Glu Ile Leu Asn Glu Ile His Leu
145                 150                 155                 160

Ile Lys Lys Asp Asp Arg Val Gly Ala Ser Glu Ala Thr Leu Leu Asn
                165                 170                 175

Met Leu Asn Ile Ser Pro Phe Ser Tyr Gly Leu Lys Ile Leu Gln Val
            180                 185                 190

Tyr Asp Ser Gly Thr Val Phe Ser Pro Asp Ile Leu Asp Ile Thr Pro
        195                 200                 205

Glu Asp Leu Arg Ser Ala Phe Val Glu Gly Val Arg Asn Val Ala Ala
    210                 215                 220

Val Ser Leu Ser Ile Gly Tyr Pro Thr Val Ala Ser Val Pro His Ser
225                 230                 235                 240

```
Ile Val Asn Gly Leu Lys Asn Leu Ile Ala Ile Ala Val Glu Thr Asp
                245                 250                 255

Ile Thr Phe Lys Glu Ala Glu Met Ala Lys Glu Tyr Leu Lys Asp Pro
            260                 265                 270

Ser Lys Phe Ala Ala Ala Ala Pro Ala Ala Gly Gly Gly Ala Ala
        275                 280                 285

Ala Ala Lys Pro Glu Glu Ser Lys Lys Glu Ala Lys Lys Glu Glu
        290                 295                 300

Ser Glu Glu Glu Asp Asp Asp Met Gly Phe Gly Leu Phe Asp
305                 310                 315

<210> SEQ ID NO 4
<211> LENGTH: 35
<212> TYPE: PRT
<213> ORGANISM: Artificial sequence
<220> FEATURE:
<223> OTHER INFORMATION: Synthetic sequence

<400> SEQUENCE: 4

Glu Tyr Leu Lys Asp Pro Ser Lys Phe Ala Ala Ala Ala Pro Ala
 1               5                  10                  15

Ala Gly Gly Gly Ala Ala Ala Ala Lys Pro Glu Glu Ser Lys Lys Glu
            20                  25                  30

Glu Ala Lys
        35

<210> SEQ ID NO 5
<211> LENGTH: 1953
<212> TYPE: DNA
<213> ORGANISM: Rhipicephalus microplus

<400> SEQUENCE: 5
atgcgtggca tcgctttgtt cgtcgccgct gtttcactga ttgtagaggg cacagcagaa      60
tcatccattt gctctgactt cgggaacgag ttctgtcgca acgctgaatg tgaagtggtg     120
cctggtgcag aggatgattt cgtgtgcaaa tgtccgcgag ataatatgta cttcaatgct     180
gctgaaaagc aatgcgaata taaagatacg tgcaagacaa gggagtgcag ctatggacgt     240
tgcgttgaaa gtaacccgag caaggctagc tgcgtctgcg aagcatcgga cgatctaacg     300
ctacaatgca aaattaaaaa tgactacgca attgactgcc gaaaccgagg tggcactgct     360
aagttgcgca cggatgggtt tattggcgca acgtgtgact gtggtgaatg gggtgcgatg     420
aacatgacca cccggaactg tgtccctacc acgtgtcttc gtcccgactt gacctgcaaa     480
gacctctgcg agaaaaacct gcttcaaagg gattctcgtt gttgccaggg gtggaacaca     540
gcaaactgtt cagccgctcc tccagctgac tcctattgct ctcctgggag ccccaaagga     600
ccggacggac agtgtataaa tgcttgcaag acgaaagaag ctgggtttgt ctgcaagcat     660
ggatgcaggt cgaccggcaa ggcgtacgag tgcacgtgcc cgagtggctc taccgtcgcc     720
gaagatggca ttacctgcaa aagtatttcg cacacagtca gctgcactgc tgagcaaaaa     780
cagacctgcc gcccaaccga agactgtcgt gtgcacaaag gaactgtgtt gtgtgagtgc     840
ccgtggaatc aacatctagt gggggacacg tgcataagtg attgcgtcga caagaaatgc     900
cacgaagaat ttatggactg tggcgtatat atgaatcgac aaagctgcta ttgtccatgg     960
aaatcaagga agccgggccc aaatgtcaac atcaatgaat gcctactgaa tgagtattac    1020
tacacggtgt cattcacccc aaacatatct tttgattctg accattgcaa atggtatgag    1080
```

```
gatcgtgttt tggaagcgat acggaccagt atcggaaaag aagtttttaa ggttgagata    1140
cttaactgca cgcaggacat taaggcaaga ctcatagcag agaaaccact gtcaaaacac    1200
gtgctcagga aactacaagc atgcgagcat ccaatcggcg aatggtgcat gatgtatccg    1260
aagttgctga tcaagaaaaa ctctgcaaca gaaatcgaag aagagaacct ttgcgacagt    1320
ctgctcaagg atcaggaagc tgcctacaaa ggtcaaaaca atgcgtcaa ggtcgacaac     1380 ctcttctggt tccagtgcgc tgatggttac acaacaactt acgagatgac acgaggtcgc    1440
ctacgccgct ccgtgtgtaa agctggagtt tcttgcaacg aaaacgagca gtcggagtgt    1500
gctgacaaag ggcaaatatt tgtttacgaa aacggcaaag cgaattgcca atgcccacca    1560
gacactaaac ctggggagat tggctgcatt gagcgtacca catgcaaccc taaagaaata    1620
caagaatgcc aagacaagaa gctggagtgc gtttacaaaa accataaagc agaatgcgag    1680
tgtcctgatg atcacgagtg ttacagggag cctgccaaag actcttgcag tgaagaggat    1740
aatggtaaat gtcaaagcag tgggcagcgt tgtgtaatag aaaacggaaa ggctgtttgc    1800
aaggaaaagt ctgaagcaac aacagctgcg actacaacaa cgaaagcgaa agacaaggat    1860
ccagatcctg gaaagtcaag tgctgcagca gtatcagcta ctgggctctt gttactgctc    1920
gcagctactt cagtcaccgc agcatcgttg taa                                 1953
```

<210> SEQ ID NO 6
<211> LENGTH: 36
<212> TYPE: PRT
<213> ORGANISM: Artificial sequence
<220> FEATURE:
<223> OTHER INFORMATION: Synthetic sequence

<400> SEQUENCE: 6

Glu Tyr Leu Lys Asp Pro Ser Lys Phe Val Ala Ala Ala Ala Ala Ala
 1               5                  10                  15

Ala Pro Ala Ala Gly Gly Gly Ala Ala Ala Lys Pro Asp Ala Lys Lys
            20                  25                  30

Glu Glu Ala Lys
        35

<210> SEQ ID NO 7
<211> LENGTH: 120
<212> TYPE: PRT
<213> ORGANISM: Artificial Sequence
<220> FEATURE:
<223> OTHER INFORMATION: Synthetic sequence

<400> SEQUENCE: 7

Gln Tyr Ile Lys Ala Asn Ser Lys Phe Ile Gly Ile Thr Glu Leu Leu
 1               5                  10                  15

Ser Glu Ile Lys Gly Val Ile Val His Arg Leu Glu Gly Val Ala Ala
            20                  25                  30

Gly Gly Gly Ala Ala Ala Ala Lys Pro Glu Glu Ser Lys Lys Glu Glu
        35                  40                  45

Ala Lys Ala Ala Gly Gly Gly Ala Ala Ala Lys Pro Glu Glu Ser
    50                  55                  60

Lys Lys Glu Glu Ala Lys Ala Ala Gly Gly Gly Ala Ala Ala Ala Lys
65                  70                  75                  80

Pro Glu Glu Ser Lys Lys Glu Glu Ala Lys Gln Tyr Ile Lys Ala Asn
                85                  90                  95

Ser Lys Phe Ile Gly Ile Thr Glu Leu Leu Ser Glu Ile Lys Gly Val
            100                 105                 110
```

```
Ile Val His Arg Leu Glu Gly Val
        115                 120

<210> SEQ ID NO 8
<211> LENGTH: 34
<212> TYPE: PRT
<213> ORGANISM: Artificial sequence
<220> FEATURE:
<223> OTHER INFORMATION: Synthetic sequence

<400> SEQUENCE: 8

Ala Tyr Leu Glu Asp Pro Ser Lys Phe Ala Val Ala Ala Ala Pro Ala
 1               5                  10                  15

Ala Gly Asn Ala Ala Pro Ala Ala Ala Ala Pro Ala Lys Val Glu Glu
            20                  25                  30

Pro Glu

<210> SEQ ID NO 9
<211> LENGTH: 35
<212> TYPE: PRT
<213> ORGANISM: Artificial sequence
<220> FEATURE:
<223> OTHER INFORMATION: Synthetic sequence

<400> SEQUENCE: 9

Glu Tyr Leu Ala Asp Pro Ser Lys Phe Ala Ser Val Ala Ala Ala Pro
 1               5                  10                  15

Ala Ala Gly Ala Thr Lys Ala Ala Ala Ala Pro Ala Lys Ala Asp
            20                  25                  30

Glu Pro Glu
        35

<210> SEQ ID NO 10
<211> LENGTH: 36
<212> TYPE: PRT
<213> ORGANISM: Artificial sequence
<220> FEATURE:
<223> OTHER INFORMATION: Synthetic sequence

<400> SEQUENCE: 10

Glu Tyr Leu Lys Asp Pro Ser Lys Phe Ala Ser Ala Ala Pro Ala Ala
 1               5                  10                  15

Ala Ser Gly Gly Gly Ala Ala Thr Lys Ala Ala Ala Pro Ala Lys Ala
            20                  25                  30

Glu Glu Pro Glu
        35

<210> SEQ ID NO 11
<211> LENGTH: 20
<212> TYPE: PRT
<213> ORGANISM: Artificial Sequence
<220> FEATURE:
<223> OTHER INFORMATION: Synthetic sequence

<400> SEQUENCE: 11

Ala Ala Gly Gly Gly Ala Ala Ala Ala Lys Pro Glu Glu Ser Lys Lys
 1               5                  10                  15

Glu Glu Ala Lys
            20

<210> SEQ ID NO 12
<211> LENGTH: 20
```

```
<212> TYPE: PRT
<213> ORGANISM: Artificial Sequence
<220> FEATURE:
<223> OTHER INFORMATION: Synthetic sequence

<400> SEQUENCE: 12

Phe Ala Ala Ala Ala Ala Pro Ala Ala Gly Gly Gly Ala Ala Ala Ala
 1               5                  10                  15

Lys Pro Glu Glu
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic sequence

<400> SEQUENCE: 13

Glu Tyr Leu Lys Asp Pro Ser Lys Phe Ala Ala Ala Ala Ala Pro Ala
 1               5                  10                  15

Ala Gly Gly Gly
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic sequence

<400> SEQUENCE: 14

Pro Ala Ala Gly Ala Thr Lys Ala Ala Ala Ala Ala Pro Ala Lys Ala
 1               5                  10                  15

Asp Glu Pro Glu
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic sequence

<400> SEQUENCE: 15

Ser Lys Phe Ala Ser Val Ala Ala Pro Ala Ala Gly Ala Thr Lys
 1               5                  10                  15

Ala Ala Ala Ala
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic sequence

<400> SEQUENCE: 16

Glu Tyr Leu Ala Asp Pro Ser Lys Phe Ala Ser Val Ala Ala Ala Pro
 1               5                  10                  15

Ala Ala Gly Ala
            20

<210> SEQ ID NO 17
```

```
<211> LENGTH: 27
<212> TYPE: DNA
<213> ORGANISM: Artificial Sequence
<220> FEATURE:
<223> OTHER INFORMATION: synthetic sequence

<400> SEQUENCE: 17
atggtcaggg aggacaagac cacctgg                                              27

<210> SEQ ID NO 18
<211> LENGTH: 28
<212> TYPE: DNA
<213> ORGANISM: Artificial Sequence
<220> FEATURE:
<223> OTHER INFORMATION: Synthetic sequence

<400> SEQUENCE: 18
ctagtcgaag agtccgaagc ccatgtcg                                             28

<210> SEQ ID NO 19
<211> LENGTH: 28
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (15)..(15)
<223> OTHER INFORMATION: n= C or G
<220> FEATURE:
<221> NAME/KEY: misc_feature
<222> LOCATION: (21)..(21)
<223> OTHER INFORMATION: n= C or G
<220> FEATURE:
<221> NAME/KEY: misc_feature
<222> LOCATION: (26)..(26)
<223> OTHER INFORMATION: n= G or A

<400> SEQUENCE: 19
atgggcaaga acacnatgat nacmcngc                                             28

<210> SEQ ID NO 20
<211> LENGTH: 29
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (5)..(5)
<223> OTHER INFORMATION: n= T or G
<220> FEATURE:
<221> NAME/KEY: misc_feature
<222> LOCATION: (6)..(6)
<223> OTHER INFORMATION: n= T or C
<220> FEATURE:
<221> NAME/KEY: misc_feature
<222> LOCATION: (13)..(13)
<223> OTHER INFORMATION: n= G or A
<220> FEATURE:
<221> NAME/KEY: misc_feature
<222> LOCATION: (18)..(18)
<223> OTHER INFORMATION: n= G or A
<220> FEATURE:
<221> NAME/KEY: misc_feature
<222> LOCATION: (19)..(19)
<223> OTHER INFORMATION: n= A or G
<220> FEATURE:
<221> NAME/KEY: misc_feature
<222> LOCATION: (21)..(21)
<223> OTHER INFORMATION: n= C or A or T
<220> FEATURE:
<221> NAME/KEY: misc_feature
```

```
<222> LOCATION: (22)..(22)
<223> OTHER INFORMATION: n= G or A
<220> FEATURE:
<221> NAME/KEY: misc_feature
<222> LOCATION: (24)..(24)
<223> OTHER INFORMATION: n= C or G

<400> SEQUENCE: 20
atggnnaggg agnacaannc nncntggaa                                          29

<210> SEQ ID NO 21
<211> LENGTH: 26
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: n= G or A
<220> FEATURE:
<221> NAME/KEY: misc_feature
<222> LOCATION: (6)..(6)
<223> OTHER INFORMATION: n= A or C or G
<220> FEATURE:
<221> NAME/KEY: misc_feature
<222> LOCATION: (9)..(9)
<223> OTHER INFORMATION: n= G or A or T
<220> FEATURE:
<221> NAME/KEY: misc_feature
<222> LOCATION: (11)..(11)
<223> OTHER INFORMATION: n= C or T
<220> FEATURE:
<221> NAME/KEY: misc_feature
<222> LOCATION: (15)..(15)
<223> OTHER INFORMATION: n= T or G or A
<220> FEATURE:
<221> NAME/KEY: misc_feature
<222> LOCATION: (21)..(21)
<223> OTHER INFORMATION: n= A or G
<220> FEATURE:
<221> NAME/KEY: misc_feature
<222> LOCATION: (24)..(24)
<223> OTHER INFORMATION: n= A or G

<400> SEQUENCE: 21
tcnaanagnc ngaancccat ntcntc                                             26
```